US007041783B2

(12) United States Patent
Reed et al.

(10) Patent No.: US 7,041,783 B2
(45) Date of Patent: May 9, 2006

(54) SURVIVIN-BINDING PROTEINS, ENCODING NUCLEIC ACIDS, AND METHODS OF USE

(75) Inventors: John C. Reed, Rancho Santa Fe, CA (US); Kazuya Okada, Isahaya (JP)

(73) Assignee: The Burnham Institute, La Jolla, CA (US)

( * ) Notice: Subject to any disclaimer, the term of this patent is extended or adjusted under 35 U.S.C. 154(b) by 452 days.

(21) Appl. No.: 10/057,813

(22) Filed: Jan. 24, 2002

(65) Prior Publication Data

US 2006/0035359 A1 Feb. 16, 2006

Related U.S. Application Data

(60) Provisional application No. 60/367,357, filed on Jan. 25, 2001.

(51) Int. Cl.
*C07K 5/00* (2006.01)
(52) U.S. Cl. .................. 530/300; 530/305; 530/324; 530/350; 435/7.1
(58) Field of Classification Search ............... 530/300, 530/350, 324, 305; 514/2; 435/7.1
See application file for complete search history.

(56) References Cited

U.S. PATENT DOCUMENTS 5,968,781 A * 10/1999 Yoon et al. ................ 435/69.7

OTHER PUBLICATIONS

Colussi, PA et al, 1998, J Biol Chem, 237(41): 26566-26570.*
Gottschalk, AR et al, 1996, Cell Death and Differentiation, 3(1): 113-118.*
Vogel MW et al, 2002, Cerbellum, 1(4): 277-87.*
Xu Xin et al, 2001, FASEB J, 15(4): A313.*
Hummler E et al, 1994, PNAS, USA, 91: 5647-5651.*
Gura (Science, 1997, 278:1041-1042).*
Jain (Sci. Am., 1994, 271:58-65).*
Curti (Crit. Rev. in Oncology/Hematology, 1993, 14:29-39).*
Hartwell et al (Science, 1997, 278:1064-1068).*
Bowie et al (Science, 1990, 257 : 1306-1310).*
Burgess et al, (Journal of Cell Biology, 1990, 11: 2129-2138).*
Lazar et al. Molecular and Cell Biology, 1988, 8: 1247-1252.*
Tao. et al. The Journal of Immunology, 1989, 143(8): 2595-2601.*
Gillies et al. Human Antibodies and Hybridomas, 1990, 1(1): 47-54.*
Tamm I et al, 1998, Cancer Res, 58: 5315-5320.*
Bourne, Y et al, 1996, Cell, 84: 863-874.*
Tsai, LH et al, 1994, Nature, 371 (6496): 419-423.*
WO200142451-A2 in MPSRCH search report, 2005, us-10-057-813-13.rng, pp. 3-4, and.*

MPSRCH search report, 2005, us-10-057-813-14.rag, pp. 1-2.*
Johnstone and Thorpe (Immunochemistry in Practice, 2nd Ed., 1987, Blackwell Scientific Publications, Oxford, pp. 49-50.*
Altieri and Marchisio, "Survivin apoptosis: an interloper between cell death and cell proliferation in cancer," *Lab. Invest.* 79:1327-1333 (1999).
Ambrosini et al., "Induction of apoptosis and inhibition of cell proliferation by survivin gene targeting," *J. Biol. Chem.* 273:11177-11182 (1998).
Ambrosini et al., "A novel anti-apoptosis gene, survivin, expressed in cancer and lymphoma," *Nat. Med.* 3:917-921 (1997).
Chai et al., "Structural and biochemical basis of apoptotic activation by Smac/DIABLO," *Nature* 406:855-862 (2000).
Du et al., "Smac, a mitochondrial protein that promotes cytochrome c-dependent caspase activation by eliminating IAP inhibition," *Cell* 102:33-42 (2000).
Grossman et al., "Inhibition of melanoma tumor growth in vivo by survivin targeting," Proc. Natl. Acad. Sci. USA 98(2):635-640 (2001).
Kobayashi et al., "Expression of a murine homologue of the inhibitior of apoptosis protein is related to cell proliferation, " *Proc. Natl. Acad. Sci. USA* 96:1457-1462 (1999).
Morgan, "Principles of CDK regulation," *Nature* 374:131-134 (1995).
Tamm et al., "IAP-family protein survivin inhibits caspase activity and apoptosis induced by Fas (CD95), Bax, caspases, and anticancer drugs," *Cancer Research* 58:5315-5320 (1998).
Verhagen et al., "Indentification of DIABLO, a mammalian protein that promotes apoptosis by binding to an antagonizing IAP proteins," *Cell* 102:43-53 (2000).
Genbank accession No.: AA313780.
Genbank accession No.: AA328484.
Genbank accession No.: AV705461.
Genbank accession No.: AW957916.
Genbank accession No.: BE790325.
Genbank accession No.: NM 017793 (gi:8923354 and gi: 8923355).

* cited by examiner

*Primary Examiner*—Susan Ungar
*Assistant Examiner*—Minh-Tam Davis
(74) *Attorney, Agent, or Firm*—McDermott Will & Emery

(57) ABSTRACT

In accordance with the present invention, there are provided novel Survivin-binding-proteins (SBPs). Nucleic acid sequences encoding such proteins and assays employing same are also disclosed. The invention SBPs can be employed in a variety of ways, for example, for the production of anti-SBP antibodies thereto, in therapeutic compositions and in bioassays methods employing such proteins and/or antibodies. Also provided are transgenic non-human mammals that express the invention protein.

9 Claims, 6 Drawing Sheets

| | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|
|  |  |  |  |  |  |  |  |  |  |  |  |  |  |  |  |  |  |  |  |  |  |  |  |  |  |  |  |  |  | SBP1 |
|  |  |  |  |  |  |  |  |  |  |  |  |  |  |  |  |  |  |  |  |  |  |  |  |  |  |  |  |  |  | Cks1(human) |
|  |  |  |  |  |  |  |  |  |  |  |  |  |  |  |  |  |  |  |  |  |  |  |  |  |  |  |  |  |  | Cks2(human) |
|  |  |  |  |  |  |  |  |  |  |  |  |  |  |  |  |  |  |  |  |  |  |  |  |  |  |  |  |  |  | Cks1(Drosophila) |
|  |  |  |  |  |  |  |  |  |  |  |  |  |  |  |  |  |  |  |  |  |  |  |  |  |  |  |  |  |  | Cks1(yeast) |

SURVIVIN-BINDING PROTEINS, ENCODING NUCLEIC ACIDS, AND METHODS OF USE

This application claims the benefit of U.S. Provisional Application No. 60/367,357, filed Jan. 25, 2001, which was converted from U.S. Ser. No. 09/770,219, and is incorporated herein by reference.

This invention was made with United States Government support under grant number AG15402 awarded by National Institutes of Health. The U.S. Government has certain rights in this invention.

The present invention relates generally to regulation of programmed cell death and more specifically to molecules that promote programmed cell death.

BACKGROUND OF THE INVENTION

In essentially all self-renewing tissues, a balance is struck between cell production by mitogenesis and cell loss due to programmed cell death, otherwise known as apoptosis, thereby maintaining total cell numbers within a physiologically appropriate range. In pathological conditions, however, the balance in cell production and cell loss can be disrupted. In cancer, for example, an increased amount of cell production due to a shortened cell cycle time or a decreased amount of cell death due to dysregulation of a programmed cell death pathway results in the growth of a tumor.

Suppression of apoptosis contributes to carcinogenesis by several mechanisms, including aberrantly prolonging the cell life span, thus facilitating the accumulation of gene mutations, permitting growth factor-independent cell survival, promoting resistance to immune-based cytotoxicity, and allowing disobeyance of cell cycle checkpoints that would normally induce apoptosis. Defects in apoptotic mechanisms also play an important role in resistance to chemotherapy and radiation.

Survivin is a recently described member of the Inhibitor of Apoptosis Protein (IAP) family of antiapoptotic proteins, which are conserved across evolution with homologues found in both vertebrate and invertebrate animal species. The baculovirus IAPs, Cp-IAP and Op-IAP, were the first members of this family to be identified based on their ability to functionally complement defects in the cell death inhibitor p35, a baculovirus protein that binds to and inhibits caspase. Subsequently, five additional human (XIAP, c-IAP1, c-IAP1, cIAP2, NAIP, and Survivin) and two *Drosophila* homologues have been identified, which have been demonstrated to inhibit cell death. A central role for IAP-family proteins in programmed cell death regulation in *Drosophila* has been suggested by the finding that several apoptosis-inducing proteins in flies, including reaper, hid, and grim bind to IAPs as part of their cytotoxic mechanism. The human IAPs (XIAP, cIAP1, and cIAP2) have been reported to bind and potently inhibit caspase-3 and -7, with Kis in the range of 0.2–10 nM. These caspases operate in the distal portions of apoptotic protease cascades, functioning as effectors rather than initiators of apoptosis.

The common structural feature of all IAP family members is a ~70 amino acid motif termed BIR, which is present in one to three copies. Using a mutagenesis approach, it was shown that the second of the three BIR domains (BIR2) of XIAP is necessary and sufficient for inhibiting certain caspase-family cell death proteases, implying that a single BIR domain can possess antiapoptotic activity. Survivin contains a single BIR domain that shares amino acid sequence similarity to the BIR2 region of XIAP.

The Survivin protein is abundantly expressed during fetal development in humans, but rarely present in adult tissues. However, expression of Survivin has been reported in most human tumors, suggesting that alterations in Survivin gene regulation occur commonly during tumorigenesis. Overexpression of Survivin in a lymphokine-dependent hematopoetic cell line has been reported to delay cell death induced by factor withdrawal. Conversely, antisense-mediated suppression of Survivin epression induces apoptosis in HcLa cells.

Most human cancers inappropriately over-express Survivin, making it one of the most tumor-specific transcripts detected to date in genome-wide surveys. Survivin has been found to be highly expressed in rapidly dividing cells but undetectable in normal differentiated tissues.

As set forth above, most IAPs bind and inhibit caspase-family cell death proteases, thus explaining their anti-apoptotic mechanism. Survivin has been reported to be associated with certain caspases, such as Caspases-3 and -7 (Tamm et al., 1998, *Canc. Res.*, 58:5315–5320), as well as shown to block apoptosis induced by over-expression of certain caspases. Survivin also binds an IAP inhibitory protein called SMAC/Diablo and may prevent it from promoting cell death (Chunying et al. 2000, *Cell*, 102:33–42; Verhagen et al., 2000, *Cell*, 102:43–53; Chai et al., 2000, *Nature*, 406:855–862). However, unlike other IAPs, Survivin expression is regulated in a cell cycle-dependent manner, with maximum levels occurring during G2/M phase, and the protein localizes to mitotic spindle microtubules and midbodies of dividing cells. Therefore, Survivin is a candidate molecule that may represent an interface between apoptosis and cell cycle regulation.

In addition to apoptosis, intereference with Survivin function by antisense methods or expression of dominant-negative mutants causes polyploidy and multinuclearity, due to a cytokinesis defect. Indeed, genetic evidence has been presented that, like mammalian Survivin, its homologues Bir1p and BIR1 in yeast and *C elegans*, respectively, play important roles in chromosome segregation and cell division during anaphase and telophase. Moreover, Survivin physically associates with the cyclin-dependent kinase cdc2 on the mitotic apparatus, and is phosphorylated on Thr34 by cdc2/cyclin B1. Over-expression of a T34A non-phosphorylatable mutant of Survivin causes massive apoptosis and polyploidy, indicating that phosphorylation of Survivin is critical for its activity as a regulator of cytokinesis and for maintaining cell survival.

A need therefore exists to identify proteins involved in the regulation of Survivin activity for therapeutic applications, including treatment of cancer. The present invention satisfies this need and provides related advantages as well.

SUMMARY OF THE INVENTION

In accordance with the present invention, there are provided novel isolated nucleic acids encoding Survivin-binding-proteins (SBPs), or functional fragments thereof. The invention also provides vectors containing invention nucleic acids and recombinant cells transformed therewith, antisense-nucleic acids thereto and related compositions. Further provided are oligonucleotides capable of hybridizing with an invention nucleic acid, such oligonucleotides further being labeled. Invention nucleic acids described herein are useful as probes for assaying an amount of SBP mRNA in a sample and for identifying nucleic acids encoding a SBP. Invention nucleic acids also are useful for expression in cells for the purposes of identifying agonists or antagonists of SBP function.

In accordance with the present invention, also provided are novel isolated Survivin-binding proteins (SBPs) having ability to bind to Survivin, cyclin, and/or cyclin-dependent kinases. Methods for expression of SBP or functional fragments thereof additionally are provided. Proteins or fragments thereof are useful in bioassays, as therapeutic compositions, and as immunogens for producing anti-SBP antibodies. Also provided are transgenic non-human mammals that express invention SBP and mutants thereof. Transgenic non-human mammals that do not express an endogenous SBP additionally are provided.

Antibodies having specific reactivity with SBP also are provided. These antibodies are useful for detecting SBP in a sample in diagnostic assays, or for identifying genes encoding proteins having similar immunoreactivity to SBP. Invention antibodies also can be used to purify a SBP from biological fluid, tissues, cells, and the like.

Methods for identifying SBP binding proteins also are provided. A method comprises contacting a sample containing a SBP binding protein and identifying the protein that binds thereto. Also provided are methods for identifying a nucleic acid molecule that binds to SBP. A method comprises contacting a sample containing nucleic acids and identifying a nucleic acid molecule that binds thereto.

Methods for modulating the activity of a protein or RNA that binds SBP also are provided. A method comprises contacting a SBP binding protein or nucleic acid molecule with a substantially pure SBP, or functional fragment thereof. A method of modulating the activity of Survivin also is provided.

Methods of treating a degenerative or hyperproliferative disorder are provided. A method of the invention employs an antisense SBP nucleic acid in an amount effective to inhibit expression of a human SBP. A method also employs SBP or functional fragment thereof or agonists or antagonists thereto administered to a subject.

BRIEF DESCRIPTION OF THE DRAWINGS

FIG. 3 shows an alignment of cyclin-dependent kinase regulatory subunit (RS) domains of SBP1 with RS domains of other proteins corresponding to human Cks1 (SEQ ID NO:3), human Cks2 (SEQ ID NO:4), Drosophila Cks1 (SEQ ID NO:5), and yeast Cks1 (SEQ ID NO:6). Identical residues are shown in black.

DETAILED DESCRIPTION OF THE INVENTION

Figure 1:
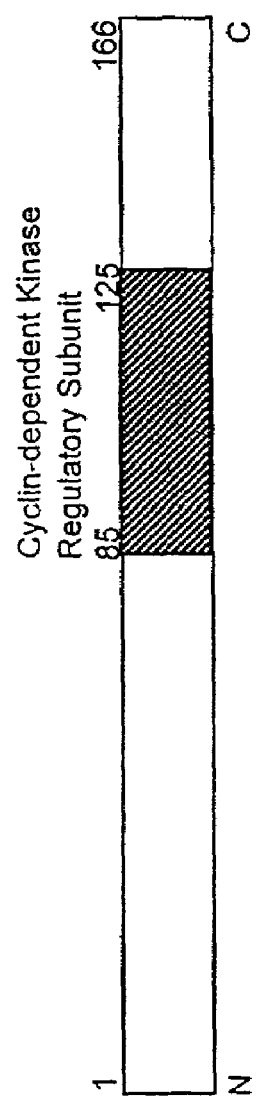
FIG. 1 shows a schematic representation of human SBP1.

In accordance with the present invention, there are provided isolated nucleic acids encoding novel mammalian Survivin binding proteins (SBPs), or functional polypeptide fragments thereof. As used herein, the term "SBP" refers to novel members of the Cks/Suc1 family of proteins (see, e.g., Morgan, DO, 1995, Nature, 374:131), wherein said SBP comprises a Survivin-binding domain. Invention SBPs are those that have the ability to bind, preferably in vivo, to at least one form of a Survivin protein (Altieri and Marchisio, 1999, Lab. Invest., 97:1327–1333), Survivin-like proteins. Invention SBPs are further characterized by comprising a cyclin-dependent kinase (cdk) regulatory domain. The term "SBP" refers to substantially pure native SBP, or recombinantly produced proteins, including naturally occurring allelic variants thereof such as mRNA generated by alternative splicing of a primary transcript, fragments thereof which retain at least one native biological activity, including an ability to bind to Survivin, an ability to bind and/or regulate a cyclin-dependent kinase, or having immunogenicity. In another embodiment, SBPs referred to herein, are those polypeptides specifically recognized by an antibody that also specifically recognizes a SBP (preferably human) including an amino acid sequence set forth in SEQ ID NO:2 or 14. Invention isolated SBPs are free of cellular components or contaminants normally associated with a native in vivo environment.

The term "biologically active" or "functional," when used herein as a modifier of an invention SEP, or polypeptide fragment thereof, refers to a polypeptide that exhibits functional characteristics similar to SEP. As disclosed herein, one function of invention SBPs is binding to Survivin. It has been found that overexpression of Survivin blocks apoptosis induced by a variety of stimuli; and that plasmids encoding antisense Survivin DNA render a tumor cell line more sensitive to cell death induced by a anticancer drugs (see, Ambrosini et al., 1997, Nature Med., 3:917–921; Ambrosini et al., 1998, J.B.C., 273:11177–11182; Tamm et al., 1998, Cancer Res., 58:5315–5320; Kobayashi et al., 1999, T. Dev. Biol., 96:1457–1462). Therefore, another function contemplated for SEP is the modulation of Survivin's function as an apoptosis regulator. SEP is also contemplated herein as having the ability to modulate the function of Survivin in its capacity as an regulator of chromosome segregation and cytokinesis.

Yet another function of SBP, via its cyclin-dependent kinase regulatory domain, is modulation of, by, or interaction with a cyclin-dependent kinase (cdk), such as for example, the enhancement of cyclin B1/cdc2 kinase activity, and the like. In this regard, it is contemplated that SBP may bridge cdk-family kinases to Survivin, facilitating the phosphorylation of Survivin, which phosphorylation modulates the function of Survivin. For example, phosphorylation of Survivin may affect its ability to bind to other proteins, such as for example, SMAC (Diablo), caspases, aurora-family kinases, or SEP. Phosphorylation might also affect the ability of Survivin to dimerize with itself. Alternatively, the binding of SBP to Survivin may affect the dimerization of Survivin irrespective of phosphorylation, either enhancing or inhibiting Survivin dimerization. Since dimerization has been shown to be critical to Survivin's functions in apoptosis and cell division, methods of modulating the binding of SBP to Survivin are useful.

Another functional activity of SBP is the ability to act as an immunogen for the production of polyclonal and monoclonal antibodies that bind specifically to an invention SBP. Thus, an invention nucleic acid encoding SEP will encode a polypeptide specifically recognized by an antibody that also specifically recognizes the SEP protein including the amino acid sequence set forth in SEQ ID NO:2 or 14. Such immunologic activity can be assayed by any method known to those of skill in the art. Therefore, SBP functional fragments include polypeptide fragments that function as immunogens for generating a SBP-specific antibody and fragments that specifically bind to a SBP-specific antibody.

The nucleic acid molecules described herein are useful for producing invention proteins, when such nucleic acids are incorporated into a variety of protein expression systems known to those of skill in the art. In addition, such nucleic acid molecules or fragments thereof can be labeled with a readily detectable substituent and used as hybridization probes for assaying for the presence and/or amount of an invention SBP gene or mRNA transcript in a given sample. The nucleic acid molecules described herein, and fragments thereof, are also useful as primers and/or templates in a PCR reaction for amplifying genes encoding invention proteins described herein.

The term "nucleic acid", also referred to as polynucleotides, encompasses ribonucleic acid (RNA) or deoxyribonucleic acid (DNA), probes, oligonucleotides, and primers and can be single stranded or double stranded. DNA can be either complementary DNA (cDNA) or genomic DNA, and can represent the sense strand, the anti-sense strand or both. Examples of nucleic acids are RNA, cDNA, or isolated genomic DNA encoding an SBP polypeptide. Such nucleic acids include, but are not limited to, nucleic acids comprising substantially the same nucleotide sequence as set forth in SEQ ID NO:1 or 13. In general, a genomic sequence of the invention includes regulatory regions such as promoters, enhancers, and introns that are outside of the exons encoding a SBP but does not include proximal genes that do not encode SBP.

Use of the terms "isolated" and/or "purified" in the present specification and claims as a modifier of DNA, RNA, polypeptides or proteins means that the DNA, RNA, polypeptides or proteins so designated have been produced in such form by the hand of man, and thus are separated from their native in vivo cellular environment.

As employed herein, the term "substantially the same nucleotide sequence" refers to DNA having sufficient identity to the reference polynucleotide, such that it will hybridize to the reference nucleotide under moderately stringent hybridization conditions. In one embodiment, DNA having substantially the same nucleotide sequence as the reference nucleotide sequence encodes substantially the same amino acid sequence as that set forth in SEQ ID NO:2 or 14. In another embodiment, DNA having "substantially the same nucleotide sequence" as the reference nucleotide sequence has at least 60% identity with respect to the reference nucleotide sequence. DNA having substantially the same nucleotide sequence can have at least 70%, at least 80%, at least 90%, at least 95%, at least 97% or at least 99% identity to the reference nucleotide sequence.

As used herein, a "modification" of a nucleic acid can also include one or several nucleotide additions, deletions, or substitutions with respect to a reference sequence. A modification of a nucleic acid can include substitutions that do not change the encoded amino acid sequence due to the degeneracy of the genetic code. Such modifications can correspond to variations that are made deliberately, or which occur as mutations during nucleic acid replication.

Exemplary modifications of the recited SBP sequences include sequences that correspond to homologs of other species, including mammalian species such as mouse, primates, including monkey and baboon, rat, rabbit, bovine, porcine, ovine, canine, feline, or other animal species. The corresponding SBP sequences of non-human species can be determined by methods known in the art, such as by PCR or by screening genomic, cDNA or expression libraries.

Another exemplary modification of the invention SBP can correspond to splice variant forms of the SBP nucleotide sequence. Additionally, a modification of a nucleotide sequence can include one or more non-native nucleotides, having, for example, modifications to the base, the sugar, or the phosphate portion, or having a modified phosphodiester linkage. Such modifications can be advantageous in increasing the stability of the nucleic acid molecule.

Furthermore, a modification of a nucleotide sequence can include, for example, a detectable moiety, such as a radiolabel, a fluorochrome, a ferromagnetic substance, a luminescent tag or a detectable binding agent such as biotin. Such modifications can be advantageous in applications where detection of a SBP nucleic acid molecule is desired.

The invention also encompasses nucleic acids which differ from the nucleic acid shown in SEQ ID NO: 1 or 13, but which have the same phenotype. Phenotypically similar nucleic acids are also referred to as "functionally equivalent nucleic acids". As used herein, the phrase "functionally equivalent nucleic acids" encompasses nucleic acids characterized by slight and non-consequential sequence variations that will function in substantially the same manner to produce the same protein product(s) as the nucleic acids disclosed herein. In particular, functionally equivalent nucleic acids encode polypeptides that are the same as those encoded by the nucleic acids disclosed herein or that have conservative amino acid variations. For example, conservative variations include substitution of a non-polar residue with another non-polar residue, or substitution of a charged residue with a similarly charged residue. These variations include those recognized by skilled artisans as those that do not substantially alter the tertiary structure of the protein.

Further provided are nucleic acids encoding SBP polypeptides that, by virtue of the degeneracy of the genetic code, do not necessarily hybridize to the invention nucleic acids under specified hybridization conditions. As used herein, the term "degenerate" refers to codons that differ in at least one nucleotide from a reference nucleic acid, but encode the same amino acids as the reference nucleic acid. Nucleic acids encoding the invention SBP polypeptides can be comprised of nucleotides that encode substantially the same amino acid sequence as set forth in SEQ ID NO:2 or 14.

The invention provides an isolated nucleic acid encoding a SBP polypeptide, or a functional fragment thereof. The invention also provides an isolated nucleic acid encoding a SBP polypeptide, or a functional fragment thereof, comprising a nucleic acid selected from:
  (a) a nucleic acid encoding a polypeptide comprising the amino acid sequence set forth in SEQ ID NO:2, or
  (b) a nucleic acid molecule comprising nucleotides 145–645 of SEQ ID NO:1, or
  (c) a nucleic acid molecule that hybridizes to the nucleic acid molecule of (a) or (b) under moderately stringent hybridization conditions, wherein said nucleic acid encodes biologically active SBP1.

Also provided is an isolated nucleic acid molecule encoding an SBP1 polypeptide, or functional fragment thereof, selected from the group consisting of:
  (a) a nucleic acid molecule encoding a polypeptide comprising amino acids 1–91 of SEQ ID NO:14, wherein said polypeptide binds Survivin;
  (b) a nucleic acid molecule encoding a polypeptide comprising amino acids 85–125 of SEQ ID NO:14, wherein said polypeptide enhances cyclin B1/cdc2 kinase activity;
  (c) a nucleic acid molecule encoding SEQ ID NO:14; and
  (d) a nucleic acid molecule that hybridizes to the complement of the nucleic acid molecule of (a), (b) or (c) under highly stringent hybridization conditions, and encodes a polypeptide that binds Survivin or enhances cyclin B1/cdc2 kinase activity.

As set forth herein, an invention SBP contains a Survivin binding domain and/or a cyclin-dependent kinase regulatory domain. Invention SBPs are contemplated herein as possessing pro-apoptotic activity.

Hybridization refers to the binding of complementary strands of nucleic acid, for example, sense:antisense strands or probe:target-nucleic acid to each other through hydrogen bonds, similar to the bonds that naturally occur in chromosomal DNA. Stringency levels used to hybridize a given probe with target-DNA can be readily varied by those of skill in the art.

The phrase "stringent hybridization" is used herein to refer to conditions under which polynucleic acid hybrids are stable. As known to those of skill in the art, the stability of hybrids is reflected in the melting temperature ($T_m$) of the hybrids. In general, the stability of a hybrid is a function of sodium ion concentration and temperature. Typically, the hybridization reaction is performed under conditions of lower stringency, followed by washes of varying, but higher, stringency. Reference to hybridization stringency relates to such washing conditions.

As used herein, the phrase "moderately stringent hybridization" refers to conditions that permit target-nucleic acid to bind a complementary nucleic acid. The hybridized nucleic acids will generally have at least about 60% identity, at least about 75% identity, at least about 85% identity; or at least about 90% identity. Moderately stringent conditions are conditions equivalent to hybridization in 50% formamide, 5× Denhart's solution, 5× SSPE, 0.2% SDS at 42° C., followed by washing in 0.2× SSPE, 0.2% SDS, at 42° C.

The phrase "high stringency hybridization" refers to conditions that permit hybridization of only those nucleic acid sequences that form stable hybrids in 0.018M NaCl at 65° C., for example, if a hybrid is not stable in 0.018M NaCl at 65° C., it will not be stable under high stringency conditions, as contemplated herein. High stringency conditions can be provided, for example, by hybridization in 50% formamide, 5× Denhart's solution, 5× SSPE, 0.2% SDS at 42° C., followed by washing in 0.1× SSPE, and 0.1% SDS at 65° C.

The phrase "low stringency hybridization" refers to conditions equivalent to hybridization in 10% formamide, 5× Denhart's solution, 6× SSPE, 0.2% SDS at 22° C., followed by washing in 1× SSPE, 0.2% SDS, at 37° C. Denhart's solution contains 1% Ficoll, 1% polyvinylpyrolidone, and 1% bovine serum albumin (BSA). 20× SSPE (sodium chloride, sodium phosphate, ethylene diamide tetraacetic acid (EDTA)) contains 3M sodium chloride, 0.2M sodium phosphate, and 0.025 M (EDTA). Other suitable moderate stringency and high stringency hybridization buffers and conditions are well known to those of skill in the art and are described, for example, in Sambrook et al., *Molecular Cloning: A Laboratory Manual,* 2nd ed., Cold Spring Harbor Press, Plainview, N.Y. (1989); and Ausubel et al., supra, 1999). Nucleic acids encoding polypeptides hybridize under moderately stringent or high stringency conditions to substantially the entire sequence, or substantial portions, for example, typically at least 15–30 nucleotides of the nucleic acid sequence set forth in SEQ ID NO:1 or 13.

The invention also provides a modification of a SBP nucleotide sequence that hybridizes to a SBP nucleic acid molecule, for example, a nucleic acid molecule referenced as SEQ ID NO:1 or 13, under moderately stringent conditions. Modifications of SBP nucleotide sequences, where the modification has at least 60% identity to a SBP nucleotide sequence, are also provided. The invention also provides modification of a SBP nucleotide sequence having at least 65% identity, at least 70% identity, at least 75% identity, at least 80% identity, at least 85% identity, at least 90% identity, or at least 95% identity.

Identity of any two nucleic acid sequences can be determined by those skilled in the art based, for example, on a BLAST 2.0 computer alignment, using default parameters. BLAST 2.0 searching is available at http://www.ncbi.nlm-.nih.gov/gorf/b12.html., as described by Tatiana et al., *FEMS Microbiol Lett.* 174:247–250 (1999); Altschul et al., *Nucleic Acids Res.,* 25:3389–3402 (1997).

One means of isolating a nucleic acid encoding a SBP polypeptide is to probe a cDNA library or genomic library with a natural or artificially designed nucleic acid probe using methods well known in the art. Nucleic acid probes derived from the SBP gene are particularly useful for this purpose. DNA and cDNA molecules that encode SBP polypeptides can be used to obtain complementary genomic DNA, cDNA or RNA from mammals, for example, human, mouse, rat, rabbit, pig, and the like, or other animal sources, or to isolate related cDNA or genomic clones by the screening of cDNA or genomic libraries, by methods well known in the art (see, for example, Sambrook et al., supra, 1989; Ausubel et al., supra, 1999).

The invention additionally provides a nucleic acid that hybridizes under high stringency conditions to the SBP coding portion of SEQ ID NO:1 or 13 corresponding to nucleotides 145–645 of SEQ ID NO:1, or corresponding to nucleotides 1–489 of SEQ ID NO:13. The invention also provides a nucleic acid having a nucleotide sequence the same or substantially the same as set that forth in SEQ ID NO:1 or 13.

The invention also provides a method for identifying nucleic acids encoding a mammalian SBP by contacting a sample containing nucleic acids with one or more SBP oligonucleotides, wherein the contacting is effected under high stringency hybridization conditions, and identifying a nucleic acid that hybridizes to the oligonucleotide. The invention additionally provides a method of detecting a SBP nucleic acid molecule in a sample by contacting the sample with two or more SBP oligonucleotides, amplifying a nucleic acid molecule, and detecting the amplification. The amplification can be performed, for example, using PCR. The invention further provides oligonucleotides that function as single stranded nucleic acid primers for amplification of a SBP nucleic acid, wherein the primers comprise a nucleic acid sequence derived from the nucleic acid sequence set forth as SEQ ID NO:1 or 13.

In accordance with a further embodiment of the present invention, optionally labeled SBP-encoding nucleic acids, or fragments thereof, can be employed to probe a library, for example, a cDNA or genomic library, and the like for additional nucleic acid sequences encoding novel SBP polypeptides. Construction of suitable cDNA libraries is well-known in the art. Screening of such a cDNA library is initially carried out under low-stringency conditions, which comprise a temperature of less than about 42° C., a formamide concentration of less than about 50%, and a moderate to low salt concentration.

Presently preferred probe-based screening conditions comprise a temperature of about 37° C., a formamide concentration of about 20%, and a salt concentration of about 5× sodium chloride, sodium citrate (SSC; 20× SSC contains 3M sodium chloride, 0.3M sodium citrate, pH 7.0). Such conditions will allow the identification of sequences having a substantial degree of similarity with the probe sequence, without requiring perfect identity. The phrase "substantial similarity" refers to sequences which share at least 50% identity. Hybridization conditions are selected which allow the identification of sequences having at least 70% identity with the probe, while discriminating against sequences having a lower degree of identity with the probe. As a result, nucleic acids having substantially the same nucleotide sequence as SEQ ID NO:1 or 13 are obtained.

As used herein, a nucleic acid "probe" is single-stranded nucleic acid, or analog thereof, that has a sequence of nucleotides that includes at least 14, at least 17, at least 20, at least 25, at least 30, at least 40, at least 50, at least 75, at least 100, at least 200, at least 300, at least 400, or at least 500 contiguous bases that are the same as (or the complement thereof) any contiguous bases set forth in SEQ ID NO:1 or 13. In another embodiment, the probe is a single stranded nucleic acid, or analog thereof, having a sequence of nucleotides of less than 14, less than 20, less than 50, less than 100, less than 200, less than 300, less than 400, or less than 500 contiguous bases that are the same as (or the complement of) any contiguous bases set forth in SEQ ID NO:1 or 13. In addition, the entire cDNA encoding region of an invention SBP, or the entire sequence corresponding to SEQ ID NO:1 or 13 can be used as a probe. Probes can be labeled by methods well-known in the art, as described hereinafter, and used, for example, in various diagnostic kits.

The invention additionally provides a SBP oligonucleotide comprising between 15 and 300 contiguous nucleotides of SEQ ID NO:1 or 13 or the anti-sense strand thereof. As used herein, the term "oligonucleotide" refers to a nucleic acid molecule that includes at least 15 contiguous nucleotides from a reference nucleotide sequence, can include at least 16, 17, 18, 19, 20 or at least 25 contiguous nucleotides, and often includes at least 30, 40, 50, 60, 70, 80, 90, 100, 125, 150, 175, 200, 225, 250, 275, 300, 325, 350, 400 or more contiguous nucleotides from the reference nucleotide sequence. The reference nucleotide sequence can be the sense strand or the anti-sense strand.

The SBP oligonucleotides of the invention that contain at least 15 contiguous nucleotides of a reference SBP nucleotide sequence are able to hybridize to SBP under moderately stringent hybridization conditions and thus can be advantageously used, for example, as probes to detect SEP DNA or RNA in a sample, and to detect splice variants thereof; as sequencing or PCR primers; as antisense reagents to block transcription of SEP RNA in cells; or in other applications known to those skilled in the art in which hybridization to a SBP nucleic acid molecule is desirable.

It is understood that a SBP nucleic acid molecule, as used herein, specifically excludes previously known nucleic acid molecules consisting of nucleotide sequences having exact sequence identity with the SBP nucleotide sequence (SEQ ID NO:1 or 13), such as Expressed Sequence Tags (ESTs), Sequence Tagged Sites (STSs) and genomic fragments, deposited in public databases such as the nr, dbest, dbsts, gss and htgs databases, which are available for searching at http://www.ncbi.nlm.nih.gov/blast/blast.cgi?Jform=0, using the program BLASTN 2.0.9 described by Altschul et al., *Nucleic Acids Res.* 25:3389–3402 (1997).

In particular, invention SEP encoding nucleic acid molecules, and invention SEP polypeptides, excludes the exact, specific and complete nucleic acid and/or amino acid sequences corresponding to any of the nucleotide and/or amino acid sequences having the Genbank (gb), NCBI, EMBL (emb) or DDBJ (dbj) accession numbers described below. NCBI accession numbers specifically excluded include NCBI ID: AW957916, AV705461, BE790325, AA313780, AA328484; GI 8923355.

The isolated SBP nucleic acid molecules of the invention can be used in a variety of diagnostic and therapeutic applications. For example, the isolated SBP nucleic acid molecules of the invention can be used as probes, as described above; as templates for the recombinant expression of SBP polypeptides; or in screening assays such as two-hybrid assays to identify cellular molecules that bind SBP.

Another useful method for producing a SBP nucleic acid molecule of the invention involves amplification of the nucleic acid molecule using PCR and SBP oligonucleotides and, optionally, purification of the resulting product by gel electrophoresis. Either PCR or RT-PCR can be used to produce a SBP nucleic acid molecule having any desired nucleotide boundaries. Desired modifications to the nucleic acid sequence can also be introduced by choosing an appropriate oligonucleotide primer with one or more additions, deletions or substitutions. Such nucleic acid molecules can be amplified exponentially starting from as little as a single gene or mRNA copy, from any cell, tissue or species of interest.

The invention thus provides methods for detecting SBP nucleic acid in a sample. The methods of detecting SBP nucleic acid in a sample can be either qualitative or quantitative, as desired. For example, the presence, abundance, integrity or structure of a SBP can be determined, as desired, depending on the assay format and the probe used for hybridization or primer pair chosen for application.

Useful assays for detecting SBP nucleic acid based on specific hybridization with an isolated SBP nucleic acid molecule are well known in the art and include, for example, in situ hybridization, which can be used to detect altered chromosomal location of the nucleic acid molecule, altered gene copy number, and RNA abundance, depending on the assay format used. Other hybridization assays include, for example, Northern blots and RNase protection assays, which can be used to determine the abundance and integrity of different RNA splice variants, and Southern blots, which can be used to determine the copy number and integrity of DNA. A SBP hybridization probe can be labeled with any suitable detectable moiety, such as a radioisotope, fluorochrome, chemiluminescent marker, biotin, or other detectable moiety known in the art that is detectable by analytical methods.

Useful assays for detecting a SBP nucleic acid in a sample based on amplifying a SBP nucleic acid with two or more SBP oligonucleotides are also well known in the art, and include, for example, qualitative or quantitative polymerase chain reaction (PCR); reverse-transcription PCR (RT-PCR); single strand conformational polymorphism (SSCP) analysis, which can readily identify a single point mutation in DNA based on differences in the secondary structure of single-strand DNA that produce an altered electrophoretic mobility upon non-denaturing gel electrophoresis; and coupled PCR, transcription and translation assays, such as a protein truncation test, in which a mutation in DNA is determined by an altered protein product on an electrophoresis gel. Additionally, the amplified SBP nucleic acid can be sequenced to detect mutations and mutational hot-spots, and specific assays for large-scale screening of samples to identify such mutations can be developed.

The invention further provides an isolated SBP polypeptide, or a functional fragment thereof, encoded by a SBP nucleic acid of the invention. For example, the invention provides a polypeptide comprising the same or substantially the same amino acid sequence as SEQ ID NO:2 or 14. Also provided is a SBP polypeptide encoded by a nucleotide sequence comprising the same or substantially the same nucleotide sequence as set forth in SEQ ID NO:1 or 13.

As employed herein, the term "substantially the same amino acid sequence" refers to amino acid sequences having at least about 70% identity with respect to the reference amino acid sequence, and retaining comparable functional and biological activity characteristic of the protein defined by the reference amino acid sequence. Preferably, proteins having "substantially the same amino acid sequence" will have at least about 80% or 85%, more preferably at least 90% amino acid identity with respect to the reference amino acid sequence; with greater than about 95%, such as 98%, 99% or greater amino acid sequence identity being especially preferred. It is recognized, however, that polypeptides, or encoding nucleic acids, containing less than the described levels of sequence identity arising as splice variants or that are modified by conservative amino acid substitutions, or by substitution of degenerate codons are also encompassed within the scope of the present invention.

Also encompassed by the term SBP are functional fragments or polypeptide analogs thereof. The term "functional fragment" refers to a peptide fragment that is a portion of a full length SBP protein, provided that the portion has a biological activity, as defined herein, that is characteristic of the corresponding full length SBP protein. Thus, the invention also provides functional fragments of invention SBP proteins, which can be identified using the binding and routine methods, such as bioassays described herein. A SBP polypeptide functional fragment can be a Survivin binding domain or a cyclin-dependent kinase regulatory domain. An exemplary functional fragment containing a Survivin binding domain is set forth as amino acids 1–91 of SEQ ID NO:2 or 14. An exemplary functional fragment containing a cyclin-dependent kinase regulatory domain is set forth as amino acids 85–125 of SEQ ID NO:2 or 14, which is contemplated herein having the ability to bind to the kinases, analogous to similar Cks/Suc1 family members.

The invention also provides a chimeric protein comprising a functional SBP domain of an invention SBP selected from the group consisting of a Survivin binding domain or a cyclin-dependent kinase regulatory domain set forth as amino acids 1–91 of SEQ ID NO:2 or 14 or amino acids 85–125 of SEQ ID NO:2 or 14, respectively. A chimeric protein comprising a SBP functional domain can be generated, for example, by recombinantly expressing a SBP functional domain fused to another polypeptide.

In another embodiment of the invention, SBP-containing chimeric proteins are provided comprising an invention SBP, or fragments thereof, having the sequence of SEQ ID NO:2 or 14, and further comprising one or more sequences from a heterologous protein. Sequences from heterologous proteins with which the SBP or functional fragment thereof are fused can include, for example, glutathione-S-transferase, an antibody, or other proteins or functional fragments thereof which facilitate recovery of the chimera. Further proteins with which the SBP or functional fragment thereof are fused will include, for example, luciferase, green fluorescent protein, an antibody, or other proteins or functional fragments thereof which facilitate identification of the chimera. Still further proteins with which the SBP or functional fragment thereof are fused will include, for example, the LexA DNA binding domain, ricin, α-sarcin, an antibody, or other proteins which have therapeutic properties or other biological activity.

As such chimeric proteins include sequences from two different proteins, the resultant amino acid sequence of the chimeric protein will typically be a non-naturally occurring sequence. Thus, in accordance with this embodiment of the invention, there are provided chimeric proteins comprising an invention SBP, or functional fragments thereof, comprising SEQ ID NO:2 or 14, or a functional fragment thereof, provided the sequence of the chimeric protein is not naturally occurring.

In another embodiment of the invention, there are provided hetero-oligomers comprising invention SBP polypeptides, or fragments thereof, invention SBP-containing proteins, SBP-containing chimeric proteins, or combinations thereof. As disclosed herein, SBP contains a Survivin binding domain, which functions to bind Survivin (Examples 5 and 6). Thus, hetero-oligomers comprising invention SBP polypeptides (SEQ ID NO:2 or 14), and fragments thereof, invention SBP-containing proteins, SBP-containing chimeric proteins, or combinations thereof, and further comprising Survivin, or SBP-binding fragments thereof, are provided.

As used herein, the term "polypeptide" when used in reference to SEP is intended to refer to a peptide or polypeptide of two or more amino acids. The term "polypeptide analog" includes any polypeptide having an amino acid residue sequence substantially the same as a sequence specifically described herein in which one or more residues have been conservatively substituted with a functionally similar residue and which displays the ability to functionally mimic a SBP as described herein. A "modification" of a SEP polypeptide also encompasses conservative substitutions of a SEP polypeptide amino acid sequence. Conservative substitutions of encoded amino acids include, for example, amino acids that belong within the following groups: (1) non-polar amino acids (Gly, Ala, Val, Leu, and Ile); (2) polar neutral amino acids (Cys, Met, Ser, Thr, Asn, and Gln); (3) polar acidic amino acids (Asp and Glu); (4) polar basic amino acids (Lys, Arg and His); and (5) aromatic amino acids (Phe, Trp, Tyr, and His). Other minor modifications are included within SBP polypeptides so long as the polypeptide retains some or all of its function as described herein.

The amino acid length of functional fragments or polypeptide analogs of the present invention can range from about 5 amino acids up to the full-length protein sequence of an invention SBP. In certain embodiments, the amino acid lengths include, for example, at least about 10 amino acids, at least about 15, at least about 20, at least about 25, at least about 30, at least about 35, at least about 40, at least about 45, at least about 50, at least about 75, at least about 100, at least about 150 or more amino acids in length up to the full-length SBP protein sequence. In other embodiments, the amino acid lengths are, for example, less than about 10 amino acids, less than about 15, less than about 20, less than about 25, less than about 30, less than about 35, less than about 40, less than about 45, less than about 50, less than about 75, less than about 100, less than about 150 or more amino acids in length up to the full-length SBP protein sequence. The functional fragments can be contiguous amino acid sequences of a SBP polypeptide, including contiguous amino acid sequences of SEQ ID NO:2 or 14.

A modification of a polypeptide can also include derivatives, analogues and functional mimetics thereof, provided that such polypeptide displays the SBP biological activity. For example, derivatives can include chemical modifications of the polypeptide such as alkylation, acylation, carbamylation, iodination, or any modification that derivatizes the polypeptide. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups can be derivatized to form salts, methyl and ethyl esters or other types of esters or hydrazides. Free hydroxyl groups can be derivatized to form O-acyl or O-alkyl derivatives. The imidazole nitrogen of histidine can be derivatized to form N-im-benzylhistidine. Also included as derivatives or analogues are those peptides which contain one or more naturally occurring amino acid derivatives of the twenty standard amino acids, for example, 4-hydroxyproline, 5-hydroxylysine, 3-methylhistidine, homoserine, ornithine or carboxyglutamate, and can include amino acids that are not linked by peptide bonds. Polypeptides of the present invention also include any polypeptide having one or more additions and/or deletions of residues, relative to the sequence of a polypeptide whose sequence is shown herein, so long as SBP activity is maintained.

A modification of a SEP polypeptide includes functional mimetics thereof. Mimetics encompass chemicals containing chemical moieties that mimic the function of the polypeptide. For example, if a polypeptide contains two charged chemical moieties having functional activity, a mimetic places two charged chemical moieties in a spatial orientation and constrained structure so that the charged chemical function is maintained in three-dimensional space. Thus, a mimetic, which orients functional groups that provide a function of SBP, are included within the meaning of a SBP derivative. All of these modifications are included within the term "polypeptide" so long as the SBP polypeptide or functional fragment retains its function.

The invention provides an isolated SBP polypeptide, or functional fragment thereof. The invention SBP polypeptides can be isolated by a variety of methods well-known in the art, for example, recombinant expression systems described herein, precipitation, gel filtration, ion-exchange, reverse-phase and affinity chromatography, and the like. Other well-known methods are described in Deutscher et al., *Guide to Protein Purification: Methods in Enzymology Vol. 182*, (Academic Press, (1990)). Alternatively, the isolated polypeptides of the present invention can be obtained using well-known recombinant methods (see, for example, Sambrook et al., supra, 1989; Ausubel et al., supra, 1999). The methods and conditions for biochemical purification of a polypeptide of the invention can be chosen by those skilled in the art, and purification monitored, for example, by an immunological assay or a functional assay.

An example of the means for preparing the invention polypeptide(s) is to express nucleic acids encoding SBP in a suitable host cell, such as a bacterial cell, a yeast cell, an amphibian cell such as an oocyte, or a mammalian cell, using methods well known in the art, and recovering the expressed polypeptide, again using well-known purification methods, so described herein. Invention polypeptides can be isolated directly from cells that have been transformed with expression vectors as described herein. Recombinantly expressed polypeptides of the invention can also be expressed as fusion proteins with appropriate affinity tags, such as glutathione S transferase (GST) or poly His, and affinity purified. The invention polypeptide, biologically functional fragments, and functional equivalents thereof can also be produced by chemical synthesis. For example, synthetic polypeptides can be produced using Applied Biosystems, Inc. Model 430A or 431A automatic peptide synthesizer (Foster City, Calif.) employing the chemistry provided by the manufacturer.

SBP polypeptides can be administered to an individual to increase an activity associated with a SBP polypeptide, including induction of apoptosis or functioning as a tumor suppressor. For example, a SBP polypeptide can be administered therapeutically to an individual using expression vectors containing nucleic acids encoding SBP polypeptides, as described below. In addition, SBP polypeptides, or a functional portion thereof, can be directly administered to an individual. Methods of administering therapeutic polypeptides are well known to those skilled in the art, for example, as a pharmaceutical composition.

In a particular embodiment, a SBP polypeptide, or functional fragment thereof, can be administered to an individual so that the SBP polypeptide or functional fragment is targeted to a tumor to induce apoptosis or otherwise function as a tumor suppressor. One method of delivering a SBP polypeptide to an intracellular target is to fuse a SBP polypeptide or functional fragment to an intracellular-targeting peptide that can penetrate the cell membrane or otherwise deliver a polypeptide to the intracellular environment such as via internalization, thereby causing the fused SBP polypeptide to enter the cell. One example of such an intracellular-targeting peptides is a fusion to the transduction domain of HIV TAT, which allows transduction of up to 100% of cells (Schwarze et al., *Science* 285:1569–1572 (1999); Vocero-Akbani et al., *Nature Med.* 5:29–33 (1999)).

Another example of such an intracellular-targeting peptide is the Antennapeida homeoprotein internalization domain (Holinger et al., *J. Biol. Chem.* 274:13298–13304 (1999)). Still another intracellular-targeting peptide is a peptide that is specific for a cell surface receptor, which allows binding and internalization of a fusion polypeptide via receptor-mediated endocytosis (Ellerby et al., *Nature Med.* 5:1032–1038 (1999)). Such intracellular-targeting peptides that mediate specific receptor interactions can be advantageously used to target a tumor (see Ellerby et al., supra, 1999). Alternatively, a SBP polypeptide of the invention can be incorporated, if desired, into liposomes, microspheres or other polymer matrices (Gregoriadis, *Liposome Technology*, Vols. I to III, 2nd ed., CRC Press, Boca Raton Fla. (1993)).

The invention additionally provides a method for modulating the activity of an oncogenic polypeptide by contacting the oncogenic polypeptide with a substantially pure SBP, or an oncogenic protein-binding fragment thereof. SBP can function to bind oncogenic proteins such as Survivin, cyclins, cyclin-dependent kinases (cdk) or cyclin/cdk complexes. Therefore, SBP or functional fragments that bind to an oncogenic protein such as Survivin, cyclins, cyclin-dependent kinases (cdk) or cyclin/cdk complexes can be used to modulate the activity of the oncogenic protein.

The present invention also provides compositions containing an acceptable carrier and any of an isolated, purified SBP mature protein or functional polypeptide fragments thereof, alone or in combination with each other. These polypeptides or proteins can be recombinantly derived, chemically synthesized or purified from native sources. As used herein, the term "acceptable carrier" encompasses any of the standard pharmaceutical carriers, such as phosphate buffered saline solution, water and emulsions such as an oil and water emulsion, and various types of wetting agents.

The invention thus provides a therapeutic composition comprising a pharmaceutically acceptable carrier and a compound selected from the group consisting of a SBP polypeptide, a functional fragment of SBP, a SBP modulating compound, and an anti-SBP antibody. The invention additionally provides a method of treating a pathology characterized by abnormal cell proliferation by administering an effective amount of the composition containing a pharmaceutically acceptable carrier and a compound selected from the group consisting of a SBP polypeptide, a functional fragment of SBP, a SBP modulating compound, and an anti-SBP antibody.

Also provided are antisense-nucleic acids having a sequence capable of binding specifically with full-length or any portion of an mRNA that encodes SBP polypeptides so as to prevent translation of the mRNA. The antisense-nucleic acid can have a sequence capable of binding specifically with any portion of the sequence of the cDNA encoding SBP polypeptides. As used herein, the phrase "binding specifically" encompasses the ability of a nucleic acid sequence to recognize a complementary nucleic acid sequence and to form double-helical segments therewith via the formation of hydrogen bonds between the complementary base pairs. An example of an antisense-nucleic acid is an antisense-nucleic acid comprising chemical analogs of nucleotides.

The present invention provides means to modulate levels of expression of SBP polypeptides by recombinantly expressing SBP anti-sense nucleic acids or employing synthetic anti-sense nucleic acid compositions (hereinafter SANC) that inhibit translation of mRNA encoding these polypeptides. Synthetic oligonucleotides, or other antisense-nucleic acid chemical structures designed to recognize and selectively bind to mRNA are constructed to be complementary to full-length or portions of an SBP coding strand, including nucleotide sequences set forth in SEQ ID NO:1 or 13.

The SANC is designed to be stable in the blood stream for administration to a subject by injection, or in laboratory cell culture conditions. The SANC is designed to be capable of passing through the cell membrane in order to enter the cytoplasm of the cell by virtue of physical and chemical properties of the SANC, which render it capable of passing through cell membranes, for example, by designing small, hydrophobic SANC chemical structures, or by virtue of specific transport systems in the cell which recognize and transport the SANC into the cell. In addition, the SANC can be designed for administration only to certain selected cell populations by targeting the SANC to be recognized by specific cellular uptake mechanisms which bind and take up the SANC only within select cell populations. In a particular embodiment the SANC is an antisense oligonucleotide.

For example, the SANC may be designed to bind to a receptor found only in a certain cell type, as discussed above. The SANC is also designed to recognize and selectively bind to target mRNA sequence, which can correspond to a sequence contained within the sequences shown in SEQ ID NO:1 or 13. The SANC is designed to inactivate target mRNA sequence by either binding thereto and inducing degradation of the mRNA by, for example, RNase I digestion, or inhibiting translation of mRNA target sequence by interfering with the binding of translation-regulating factors or ribosomes, or inclusion of other chemical structures, such as ribozyme sequences or reactive chemical groups which either degrade or chemically modify the target mRNA. SANCs have been shown to be capable of such properties when directed against mRNA targets (see Cohen et al., *TIPS*, 10:435 (1989) and Weintraub, *Sci. American*, January (1990), pp. 40).

The invention further provides a method of modulating the level of apoptosis in a cell by introducing an antisense nucleotide sequence into the cell, wherein the antisense nucleotide sequence specifically hybridizes to a nucleic acid molecule encoding a SBP, wherein the hybridization reduces or inhibits the expression of the SBP in the cell. The use of anti-sense nucleic acids, including recombinant anti-sense nucleic acids or SANCs, can be advantageously used to inhibit cell death.

Compositions comprising an amount of the antisense-nucleic acid of the invention, effective to reduce expression of SBP polypeptides by entering a cell and binding specifically to mRNA encoding SBP polypeptides so as to prevent translation and an acceptable hydrophobic carrier capable of passing through a cell membrane are also provided herein. Suitable hydrophobic carriers are described, for example, in U.S. Pat. Nos. 5,334,761; 4,889,953; 4,897,355, and the like. The acceptable hydrophobic carrier capable of passing through cell membranes may also comprise a structure which binds to a receptor specific for a selected cell type and is thereby taken up by cells of the selected cell type. For example, the structure can be part of a protein known to bind to a cell-type specific receptor such as a tumor.

Antisense-nucleic acid compositions are useful to inhibit translation of mRNA encoding invention polypeptides. Synthetic oligonucleotides, or other antisense chemical structures are designed to bind to mRNA encoding SBP polypeptides and inhibit translation of mRNA and are useful as compositions to inhibit expression of SBP associated genes in a tissue sample or in a subject.

The invention also provides a method for expression of a SBP polypeptide by culturing cells containing a SBP nucleic acid under conditions suitable for expression of SBP. Thus, there is provided a method for the recombinant production of a SBP of the invention by expressing the nucleic acid sequences encoding SBP in suitable host cells. Recombinant DNA expression systems that are suitable to produce SBP described herein are well-known in the art (see, for example, Ausubel et al., supra, 1999). For example, the above-described nucleotide sequences can be incorporated into vectors for further manipulation. As used herein, vector refers to a recombinant DNA or RNA plasmid or virus containing discrete elements that are used to introduce heterologous DNA into cells for either expression or replication thereof.

The invention also provides vectors containing the SBP nucleic acids of the invention. Suitable expression vectors are well-known in the art and include vectors capable of expressing nucleic acid operatively linked to a regulatory sequence or element such as a promoter region or enhancer region that is capable of regulating expression of such nucleic acid. Appropriate expression vectors include those that are replicable in eukaryotic cells and/or prokaryotic cells and those that remain episomal or those which integrate into the host cell genome.

Promoters or enhancers, depending upon the nature of the regulation, can be constitutive or regulated. The regulatory sequences or regulatory elements are operatively linked to a nucleic acid of the invention such that the physical and functional relationship between the nucleic acid and the regulatory sequence allows transcription of the nucleic acid.

Suitable vectors for expression in prokaryotic or eukaryotic cells are well known to those skilled in the art (see, for example, Ausubel et al., supra, 1999). Vectors useful for expression in eukaryotic cells can include, for example, regulatory elements including the SV40 early promoter, the cytomegalovirus (CMV) promoter, the mouse mammary tumor virus (MMTV) steroid-inducible promoter, Moloney murine leukemia virus (MMLV) promoter, and the like. The vectors of the invention are useful for subcloning and amplifying a SBP nucleic acid molecule and for recombinantly expressing a SBP polypeptide. A vector of the invention can include, for example, viral vectors such as a bacteriophage, a baculovirus or a retrovirus; cosmids or plasmids; and, particularly for cloning large nucleic acid molecules, bacterial artificial chromosome vectors (BACs) and yeast artificial chromosome vectors (YACs). Such vectors are commercially available, and their uses are well known in the art. One skilled in the art will know or can readily determine an appropriate promoter for expression in a particular host cell.

The invention additionally provides recombinant cells containing SBP nucleic acids of the invention. The recombinant cells are generated by introducing into a host cell a vector containing a SBP nucleic acid molecule. The recombinant cells are transducted, transfected or otherwise genetically modified. Exemplary host cells that can be used to express recombinant SEP molecules include mammalian primary cells; established mammalian cell lines, such as COS, CHO, HeLa, NIH3T3, HEK 293 and PC12 cells; amphibian cells, such as *Xenopus* embryos and oocytes; and other vertebrate cells. Exemplary host cells also include insect cells such as *Drosophila* and *Spodoptera frugiperda* (e.g. for use in well-known baculovirus expression systems, such as described in Murakimi et al., 2001, *Cytokine*, 13(1):18–24, and the like), yeast cells such as *Saccharomyces cerevisiae, Saccharomyces pombe*, or *Pichia pastoris*, and prokaryotic cells such as *Escherichia coli*.

In one embodiment, nucleic acids encoding the invention SEP polypeptides can be delivered into mammalian cells, either in vivo or in vitro using suitable vectors well-known in the art. Suitable vectors for delivering a SEP polypeptide, or a functional fragment thereof to a mammalian cell, include viral vectors such as retroviral vectors, adenovirus, adeno-associated virus, lentivirus, herpesvirus, as well as non-viral vectors such as plasmid vectors. Such vectors are useful for providing therapeutic amounts of a SEP polypeptide (see, for example, U.S. Pat. No. 5,399,346, issued Mar. 21, 1995). Delivery of SEP polypeptides or nucleic acids therapeutically can be particularly useful when targeted to a tumor cell, thereby inducing apoptosis in tumor cells. In addition, where it is desirable to limit or reduce the in vivo expression of the invention SEP, the introduction of the antisense strand of the invention nucleic acid is contemplated.

Viral based systems provide the advantage of being able to introduce relatively high levels of a heterologous nucleic acid into a variety of cells. Additionally, such viruses can introduce heterologous DNA into nondividing cells. Suitable viral vectors for introducing invention nucleic acid encoding an SBP protein into mammalian cells (e.g., vascular tissue segments) are well known in the art. These viral vectors include, for example, Herpes simplex virus vectors (U.S. Pat. No. 5,501,979), Vaccinia virus vectors (U.S. Pat. No. 5,506,138), Cytomegalovirus vectors (U.S. Pat. No. 5,561,063), Modified Moloney murine leukemia virus vectors (U.S. Pat. No. 5,693,508), adenovirus vectors (U.S. Pat. Nos. 5,700,470 and 5,731,172), adeno-associated virus vectors (U.S. Pat. No. 5,604,090), constitutive and regulatable retrovirus vectors (U.S. Pat. Nos. 4,405,712; 4,650,764 and 5,739,018, respectively), papilloma virus vectors (U.S. Pat. Nos. 5,674,703 and 5,719,054), and the like. Especially preferred viral vectors are the adenovirus and retroviral vectors.

For example, in one embodiment of the present invention, adenovirus-transferrin/polylysine-DNA (TfAdpl-DNA) vector complexes (Wagner et al., *Proc. Natl. Acad. Sci., USA*, 89:6099–6103 (1992); Curiel et al., *Hum. Gene Ther.*, 3:147–154 (1992); Gao et al., *Hum. Gene Ther.*, 4:14–24 (1993)) are employed to transduce mammalian cells with heterologous SBP nucleic acid. Any of the plasmid expression vectors described herein may be employed in a TfAdpl-DNA complex.

Vectors useful for therapeutic administration of a SBP polypeptide of nucleic acid can contain a regulatory element that provides tissue specific or inducible expression of an operatively linked nucleic acid. One skilled in the art can readily determine an appropriate tissue-specific promotor or enhancer that allows exparssion of a SBP polypeptide or nucleic acid in a desired tissue. Any of a variety of inducible promoters or enhancers can also be included in the vector for regulatable expression of a SBP polypeptide or nucleic acid. Such inducible systems, include, for example, tetracycline inducible system (Gossen & Bizard, *Proc. Natl. Acad. Sci. USA*, 89:5547–5551 (1992); Gossen et al., *Science*, 268: 1766–1769 (1995); Clontech, Palo Alto, Calif.); metalothionein promoter induced by heavy metals; insect steroid hormone responsive to ecdysone or related steroids such as muristerone (No et al., *Proc. Natl. Acad. Sci. USA*, 93:3346–3351 (1996); Yao et al., *Nature*, 366:476–479 (1993); Invitrogen, Carlsbad, Calif.); mouse mammory tumor virus (MMTV) induced by steroids such as glucocortocoid and estrogen (Lee et al., Nature, 294:228–232 (1981); and heat shock promoters inducible by temperature changes.

An inducible system particularly useful for therapeutic administration utilizes an inducible promotor that can be regulated to deliver a level of therapeutic product in response to a given level of drug administered to an individual and to have little or no expression of the therapeutic product in the absence of the drug. One such system utilizes a Gal4 fusion that is inducible by an antiprogestin such as mifepristone in a modified adenovirus vector (Burien et al., *Proc. Natl. Acad. Sci. USA*, 96:355–360 (1999). Another such inducible system utilizes the drug rapamycin to induce reconstitution of a transcriptional activator containing rapamycin binding domains of FKBP12 and FRAP in an adeno-associated virus vector (Ye et al., *Science*, 283:88–91 (1999)). It is understood that any combination of an inducible system can be combined in any suitable vector, including those disclosed herein. Such a regulatable inducible system is advantageous because the level of expression of the therapeutic product can be controlled by the amount of drug administered to the individual or, if desired, expression of the therapeutic product can be terminated by stopping administration of the drug.

The invention additionally provides an isolated anti-SBP antibody having specific reactivity with a SBP. The anti-SBP antibody can be a monoclonal antibody or a polyclonal antibody. The invention further provides cell lines producing monoclongal antibodies having specific reactivity with a SBP.

The invention thus provides antibodies that specifically bind a SBP polypeptide. As used herein, the term "antibody"

is used in its broadest sense to include polyclonal and monoclonal antibodies, as well as antigen binding fragments of such antibodies. With regard to an anti-SBP antibody of the invention, the term "antigen" means a native or synthesized SBP polypeptide or fragment thereof. An anti-SBP antibody, or antigen binding fragment of such an antibody, is characterized by having specific binding activity for a SBP polypeptide or a peptide portion thereof of at least about $1 \times 10^5$ M-1. Thus, Fab, F(ab')$_2$, Fd and Fv fragments of an anti-SBP antibody, which retain specific binding activity for a SBP polypeptide, are included within the definition of an antibody. Specific binding activity of a SBP polypeptide can be readily determined by one skilled in the art, for example, by comparing the binding activity of an anti-SBP antibody to a SBP polypeptide versus a control polypeptide that is not a SBP polypeptide. Methods of preparing polyclonal or monoclonal antibodies are well known to those skilled in the art (see, for example, Harlow and Lane, *Antibodies: A Laboratory Manual*, Cold Spring Harbor Laboratory Press (1988)).

In addition, the term "antibody" as used herein includes naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains as described by Huse et al. (*Science* 246:1275–1281 (1989)). These and other methods of making, for example, chimeric, humanized, CDR-grafted, single chain, and bifunctional antibodies are well known to those skilled in the art (Winter and Harris, *Immunol. Today* 14:243–246 (1993); Ward et al., *Nature* 341:544–546 (1989); Harlow and Lane, supra, 1988; Hilyard et al., *Protein Engineering: A practical approach* (IRL Press 1992); Borrabeck, *Antibody Engineering,* 2d ed. (Oxford University Press 1995)).

Anti-SBP antibodies can be raised using a SBP immunogen such as an isolated SBP polypeptide having the amino acid sequence of SEQ ID NO:2 or 14, or a fragment thereof, which can be prepared from natural sources or produced recombinantly, or a peptide portion of the SBP polypeptide. Such peptide portions of a SBP polypeptide are functional antigenic fragments if the antigenic peptides can be used to generate a SBP-specific antibody. A non-immunogenic or weakly immunogenic SBP polypeptide or portion thereof can be made immunogenic by coupling the hapten to a carrier molecule such as bovine serum albumin (BSA) or keyhole limpet hemocyanin (KLH). Various other carrier molecules and methods for coupling a hapten to a carrier molecule are well known in the art (see, for example, Harlow and Lane, supra, 1988). An immunogenic SBP polypeptide fragment can also be generated by expressing the peptide portion as a fusion protein, for example, to glutathione S transferase (GST), polyHis or the like. Methods for expressing peptide fusions are well known to those skilled in the art (Ausubel et al., *Current Protocols in Molecular Biology* (Supplement 47), John Wiley & Sons, New York (1999)).

The invention further provides a method for detecting the presence of a human SBP in a sample by contacting a sample with a SBP-specific antibody, and detecting the presence of specific binding of the antibody to the sample, thereby detecting the presence of a human SBP in the sample. SBP specific antibodies can be used in diagnostic methods and systems to detect the level of SBP present in a sample. As used herein, the term "sample" is intended to mean any biological fluid, cell, tissue, organ or portion thereof, that includes or potentially includes SBP nucleic acids or polypeptides. The term includes samples present in an individual as well as samples obtained or derived from the individual. For example, a sample can be a histologic section of a specimen obtained by biopsy, or cells that are placed in or adapted to tissue culture. A sample further can be a subcellular fraction or extract, or a crude or substantially pure nucleic acid or protein preparation.

SBP-specific antibodies can also be used for the immunoaffinity or affinity chromatography purification of the invention SBP. In addition, methods are contemplated herein for detecting the presence of an invention SBP protein in a cell, comprising contacting the cell with an antibody that specifically binds to SBP polypeptides under conditions permitting binding of the antibody to the SBP polypeptides, detecting the presence of the antibody bound to the SBP polypeptide, and thereby detecting the presence of invention polypeptides in a cell. With respect to the detection of such polypeptides, the antibodies can be used for in vitro diagnostic or in vivo imaging methods.

Immunological procedures useful for in vitro detection of target SBP polypeptides in a sample include immunoassays that employ a detectable antibody. Such immunoassays include, for example, immunohistochemistry, immunofluorescence, ELISA assays, radioimmunoassay, FACS analysis, immunoprecipitation, immunoblot analysis, Pandex microfluorimetric assay, agglutination assays, flow cytometry and serum diagnostic assays, which are well known in the art (Harlow and Lane, supra, 1988; Harlow and Lane, *Using Antibodies: A Laboratory Manual*, Cold Spring Harbor Press (1999)).

An antibody can be made detectable by various means well known in the art. For example, a detectable marker can be directly attached to the antibody or indirectly attached using, for example, a secondary agent that recognizes the SBP specific antibody. Useful markers include, for example, radionucleotides, enzymes, binding proteins such as biotin, fluorogens, chromogens and chemiluminescent labels.

As used herein, the terms "label" and "indicating means" in their various grammatical forms refer to single atoms and molecules that are either directly or indirectly involved in the production of a detectable signal. Any label or indicating means can be linked to invention nucleic acid probes, expressed proteins, polypeptide fragments, or antibody molecules. These atoms or molecules can be used alone or in conjunction with additional reagents. Such labels are themselves well-known in clinical diagnostic chemistry.

The labeling means can be a fluorescent labeling agent that chemically binds to antibodies or antigens without denaturation to form a fluorochrome (dye) that is a useful immunofluorescent tracer. A description of immunofluorescent analytic techniques is found in DeLuca, "Immunofluorescence Analysis", in *Antibody As a Tool*, Marchalonis et al., eds., John Wiley & Sons, Ltd., pp. 189–231 (1982), which is incorporated herein by reference.

In one embodiment, the indicating group is an enzyme, such as horseradish peroxidase (HRP), glucose oxidase, and the like. In another embodiment, radioactive elements are employed labeling agents. The linking of a label to a substrate, i.e., labeling of nucleic acid probes, antibodies, polypeptides, and proteins, is well known in the art. For instance, an invention antibody can be labeled by metabolic incorporation of radiolabeled amino acids provided in the culture medium. See, for example, Galfre et al., *Meth.*

*Enzymol.,* 73:3–46 (1981). Conventional means of protein conjugation or coupling by activated functional groups are particularly applicable. See, for example, Aurameas et al., *Scand. J. Immunol., Vol.* 8, Suppl. 7:7–23 (1978), Rodwell et al., *Biotech.,* 3:889–894 (1984), and U.S. Pat. No. 4,493, 795.

In addition to detecting the presence of a SBP polypeptide, invention anti-SBP antibodies are contemplated for use herein to modulate the activity of the SBP polypeptide in living animals, in humans, or in biological tissues or fluids isolated therefrom. The term "modulate" refers to a compound's ability to increase the biological activity by functioning as an agonist or inhibit the biological activity by functioning as an antagonist of an invention SBP polypeptide. Accordingly, compositions comprising a carrier and an amount of an antibody having specificity for SBP polypeptides effective to block naturally occurring ligands or other SBP-binding proteins from binding to invention SBP polypeptides are contemplated herein. For example, a monoclonal antibody directed to an epitope of an invention SBP polypeptide, including an amino acid sequence set forth in SEQ ID NO:2 or 14, can be useful for this purpose.

The present invention further provides transgenic non-human mammals that are capable of expressing exogenous nucleic acids encoding SBP polypeptides. As employed herein, the phrase "exogenous nucleic acid" refers to nucleic acid sequence which is not native to the host, or which is present in the host in other than its native environment, for example, as part of a genetically engineered DNA construct. In addition to naturally occurring levels of SBP, a SBP polypeptide of the invention can either be overexpressed or underexpressed in transgenic mammals, for example, underexpressed in a knock-out animal.

Also provided are transgenic non-human mammals capable of expressing nucleic acids encoding SBP polypeptides so mutated as to be incapable of normal activity. Therefore, the transgenic non-human mammals do not express native SBP or have reduced expression of native SBP. The present invention also provides transgenic non-human mammals having a genome comprising antisense nucleic acids complementary to nucleic acids encoding SBP polypeptides, placed so as to be transcribed into antisense mRNA complementary to mRNA encoding SBP polypeptides, which hybridizes to the mRNA and, thereby, reduces the translation thereof. The nucleic acid can additionally comprise an inducible promoter and/or tissue specific regulatory elements, so that expression can be induced, or restricted to specific cell types.

Animal model systems useful for elucidating the physiological and behavioral roles of SBP polypeptides are also provided, and are produced by creating transgenic animals in which the expression of the SBP polypeptide is altered using a variety of techniques. Examples of such techniques include the insertion of normal or mutant versions of nucleic acids encoding an SBP polypeptide by microinjection, retroviral infection or other means well known to those skilled in the art, into appropriate fertilized embryos to produce a transgenic animal, see, for example, Hogan et al., *Manipulating the Mouse Embryo: A Laboratory Manual* (Cold Spring Harbor Laboratory, (1986)). Transgenic animal model systems are useful for in vivo screening of compounds for identification of specific ligands, such as agonists or antagonists, which activate or inhibit a biological activity.

Also contemplated herein, is the use of homologous recombination of mutant or normal versions of SEP genes with the native gene locus in transgenic animals, to alter the regulation of expression or the structure of SEP polypeptides by replacing the endogeneous gene with a recombinant or mutated SBP gene. Methods for producing a transgenic non-human mammal including a gene knock-out non-human mammal, are well known to those skilled in the art (see, Capecchi et al., *Science* 244:1288 (1989); Zimmer et al., *Nature* 338:150 (1989); Shastry, *Experentia,* 51:1028–1039 (1995); Shastry, *Mol. Cell. Biochem.,* 181:163–179 (1998); and U.S. Pat. No. 5,616,491, issued Apr. 1, 1997, No. 5,750,826, issued May 12, 1998, and U.S. Pat. No. 5,981, 830, issued Nov. 9, 1999).

Invention nucleic acids, oligonucleotides, including antisense, vectors containing invention nucleic acids, transformed host cells, polypeptides and combinations thereof, as well as antibodies of the present invention, can be used to screen compounds to determine whether a compound functions as a potential agonist or antagonist of invention polypeptides. These screening assays provide information regarding the function and activity of invention polypeptides, which can lead to the identification and design of compounds that are capable of specific interaction with one or more types of polypeptides, peptides or proteins.

Thus, the invention provides methods for identifying compounds which bind to SBP polypeptides. The invention proteins can be employed in a competitive binding assay. Such an assay can accommodate the rapid screening of a large number of compounds to determine which compounds, if any, are capable of binding to SBP polypeptides. Subsequently, more detailed assays can be carried out with those compounds found to bind, to further determine whether such compounds act as modulators, agonists or antagonists of invention SBP polypeptides. Compounds that bind to and/or modulate invention SBP polypeptides can be used to treat a variety of pathologies mediated by invention SBP polypeptides.

Various binding assays to identify cellular proteins that interact with protein binding domains are known in the art and include, for example, yeast two-hybrid screening assays (see, for example, U.S. Pat. Nos. 5,283,173, 5,468,614 and 5,667,973; Ausubel et al., supra, 1999; Luban et al., *Curr. Opin. Biotechnol.* 6:59–64 (1995)) and affinity column chromatography methods using cellular extracts. By synthesizing or expressing polypeptide fragments containing various SBP sequences or deletions, the SBP binding interface can be readily identified.

In another embodiment of the invention, there is provided a bioassay for identifying compounds which modulate the activity of invention SBP polypeptides. According to this method, invention polypeptides are contacted with an "unknown" or test substance, for example, in the presence of a reporter gene construct responsive to a SBP signaling pathway, the activity of the polypeptide is monitored subsequent to the contact with the "unknown" or test substance, and those substances which cause the reporter gene construct to be expressed are identified as functional ligands for SBP polypeptides. Such reporter gene assays and systems are well known to those skilled in the art (Ausubel et al., supra, 1999). In addition, a reporter gene constrict can be generated using the promoter region of SBP and screened for compounds that increase or decrease SBP gene promoter activity. Such compounds can also be used to alter SBP expression.

In accordance with another embodiment of the present invention, transformed host cells that recombinantly express invention polypeptides can be contacted with a test compound, and the modulating effect(s) thereof can then be evaluated by comparing the SBP-mediated response, for example, via reporter gene expression in the presence and absence of test compound, or by comparing the apoptotic or cytokinetic response of test cells or control cells, to the presence of the compound.

As used herein, a compound or a signal that "modulates the activity" of invention polypeptides refers to a compound or a signal that alters the activity of SBP polypeptides, such as apoptosis regulation, kinase regulation, cell segregation regulation, cytokinesis regulation, cyclin-binding, Survivin-binding, so that the activity of the invention polypeptide is different in the presence of the compound or signal than in the absence of the compound or signal. In particular, such compounds or signals include agonists and antagonists. An agonist encompasses a compound or a signal that activates SBP protein expression or biological activity. Alternatively, an antagonist includes a compound or signal that interferes with SBP expression or biological activity. Typically, the effect of an antagonist is observed as a blocking of agonist-induced protein activation. Antagonists include competitive and non-competitive antagonists.

Assays to identify compounds that modulate SBP polypeptide expression can involve detecting a change in SBP polypeptide abundance in response to contacting the cell with a compound that modulates SBP activity. Assays for detecting changes in polypeptide expression include, for example, immunoassays with SBP-specific SBP antibodies, such as immunoblotting, immunofluorescence, immunohistochemistry and immunoprecipitation assays, as described above.

As understood by those of skill in the art, assay methods for identifying compounds that modulate SBP activity generally require comparison to a control. One type of a "control" is a cell or culture that is treated substantially the same as the test cell or test culture exposed to the compound, with the distinction that the "control" cell or culture is not exposed to the compound. Another type of "control" cell or culture can be a cell or culture that is identical to the test cells, with the exception that the "control" cells or culture do not express a SBP polypeptide. Accordingly, the response of the transfected cell to a compound is compared to the response, or lack thereof, of the "control" cell or culture to the same compound under the same reaction conditions.

Methods for producing pluralities of compounds to use in screening for compounds that modulate the activity of a SBP polypeptide, including chemical or biological molecules such as simple or complex organic molecules, metal-containing compounds, carbohydrates, peptides, proteins, peptidomimetics, glycoproteins, lipoproteins, nucleic acids, antibodies, and the like, are well known in the art and are described, for example, in Huse, U.S. Pat. No. 5,264,563; Francis et al., *Curr. Opin. Chem. Biol.* 2:422–428 (1998); Tietze et al., *Curr. Biol.*, 2:363–371 (1998); Sofia, *Mol. Divers.* 3:75–94 (1998); Eichler et al., *Med. Res. Rev.* 15:481–496 (1995); and the like. Libraries containing large numbers of natural and synthetic compounds also can be obtained from commercial sources. Combinatorial libraries of molecules can be prepared using well known combinatorial chemistry methods (Gordon et al., *J. Med. Chem.* 37: 1233–1251 (1994); Gordon et al., *J. Med. Chem.* 37: 1385–1401 (1994); Gordon et al., *Acc. Chem. Res.* 29:144–154 (1996); Wilson and Czarnik, eds., *Combinatorial Chemistry: Synthesis and Application*, John Wiley & Sons, New York (1997)).

Compounds that modulate SBP activity can be screened by the methods disclosed herein to identify compounds that modulate any biological activity or function of SEP. For example, compounds can be identified that alter the binding interaction of SEP with Survivin, thereby modulating apoptosis, chromosome segregation and/or cytokinesis. Additionally, compounds can be identified that modulate cyclin-dependent kinase activity associated with SEP. For example, it has been found that Cdc2 kinase phosphorylates threonine 34 on Survivin, and this phosphorylation is required for Survivin's functions (Grossman et al., Jan. 9, 2001, *Proc. Natl. Acad. Sci. USA*). It has also been found that mutants lacking this phosphorylation site (threonine 34) induce cell cycle arrest and apoptosis when expressed in cancer cell lines. Accordingly, methods of inhibiting Survivin phosphorylation are contemplated herein as useful to promote apoptosis.

In this regard, it is contemplated that SBP may bridge cdk-family kinases to Survivin, facilitating the phosphorylation of Survivin, which phosphorylation modulates the function of Survivin. For example, phosphorylation of Survivin may affect its ability to bind to other proteins, such as for example, SMAC (Diablo), caspases, aurora-family kinases, or SBP. Phosphorylation might also affect the ability of Survivin to dimerize with itself. Alternatively, the binding of SBP to Survivin may affect the dimerization of Survivin irrespective of phosphorylation, either enhancing or inhibiting Survivin dimerization. Since dimerization has been shown to be critical to Survivin's functions in apoptosis and cell division (e.g., chromosome segregation and cytokinesis), invention methods of modulating the binding of SBP to Survivin are useful to modulate, preferably inhibit, apoptosis, thereby treating various cancers.

For example, It has been found that the overexpression of Survivin is one mechanism of delaying cell death (Ambrosini et al., 1997, *Nat. Med.*, 3:917–921). Therefore, compounds that modulate survivin binding activity of SBP can be used to alter apoptosis, thereby increasing or decreasing apoptotic activity of SBP.

In yet another embodiment of the present invention, the activation of SBP polypeptides can be modulated by contacting the polypeptides with an effective amount of at least one compound identified by the assays described herein. The invention also provides a method of identifying an effective agent that alters the association of a SBP with a SBP-Associated-polypeptide (SAP). The method includes the steps of contacting the SBP and the SAP polypeptide, under conditions that allow said SBP and SAP polypeptide to associate, with a compound; and detecting the altered association of the SBP and SAP polypeptide, thereby identifying a compound that is an effective agent for altering the association of SBP with SAP. The compound can be, for example, a drug or polypeptide. A SAP can be, for example, a IAP (Inhibitor of Apoptosis Protein) family member, such as Survivin; a Suc1/cks kinase family member, such as Cdc2 kinase, a cyclin, cyclin/cdk complex, or the like.

As disclosed herein, SBP is a new member of the Cks/Suc1 family of proteins that is contemplated herein as having cyclin and/or "cyclin/cdk complex" binding activity, by virtue of its cyclin-dependent kinase regulatory domain set forth as amino acids 85–125 of SEQ ID NO:2 or 14. Other cks/Suc1 regulatory domains are known to bind Cdk/Cyclin complexes and to regulate kinase activity. Therefore, modulation of SBP activity can be advantageously used to modulate the targeting of cyclin-dependent kinases (cdks), such as Cdc2, or cylin/cdk complexes, such as to Survivin, thereby modulating the phosphorylation of Survivin. For example, decreasing or inhibiting molecular bridging activity of SBP between a cdk and Survivin can be used to inhibit Survivin phosporylation, thereby promoting apoptosis in a cell, which is useful for treating cell proliferation disorders, such as cancer, and the like. SBP activity can be decreased, for example, by delivering to a cell an antisense nucleic acid encoding SBP such that expression of SBP is inhibited. Additionally, SBP activity can be decreased by using a modulatory agent that functions as an antagonist. Promoting apoptosis by decreasing SBP and/or Survivin activity or expression is useful, for example, in therapeutic applications such as the treatment of cancer.

In addition, an agonist of SBP activity can be identified by the methods disclosed herein and used to increase SBP activity. Increasing SBP activity can be used to inhibit apoptosis. Inhibiting apoptosis can be useful, for example, to treat various diseases or pathologies. For example, decreasing SBP activity with anti-sense nucleic acids or small molecule compounds can be used to treat stroke, heart attack, autoimmunity, trauma, neuron cell death, and inflammatory diseases, including Crohn's disease.

The invention further provides a method for modulating an activity mediated by a SBP polypeptide by contacting the SBP polypeptide with an effective, modulating amount of an agent that modulates SBP activity. The SBP activity can be, for example, apoptosis-modulating activity, such as apoptosis-inhibiting activity; binding to Survivin; binding to a cyclin-dependent kinase, such as Cdc2; binding to a cyclin/cdk complex; binding to cyclin; or the like. The invention additionally provides a method of modulating the level of apoptosis in a cell. The method includes the steps of introducing a nucleic acid molecule encoding SBP into the cell; and expressing the SBP in the cell, wherein the expression of the SBP modulates apoptosis in the cell.

The invention further provides a method of modulating the level of apoptosis in a cell by contacting the cell with a compound that effectively alters the association of SBP with a SBP-associated-protein in the cell, or that effectively alters the activity of a SBP in the cell. Additionally provided by the invention is a method of modulating interactions between SBP and Survivin or cyclin-dependent kinase by contacting a SBP polypeptide with the agent that inhibits or alters interactions between SBP and Survivin or cyclin-dependent kinase.

As disclosed herein, methods using SBP nucleic acids or antibodies can be used as a diagnostic for predisposition or progression of cancer, for example, leukemia, prostate, ovarian cancer, and the like. Changes in SBP expression or activity can be correlated with patient survival or response to therapy, and a correlation can be used to monitor cancer progression or response to therapy.

The invention further provides a method of diagnosing a pathology characterized by an increased or decreased level of a SBP in a subject. The method includes the steps of (a) obtaining a test sample from the subject; (b) contacting the sample with an agent that can bind the SBP under suitable conditions, wherein the conditions allow specific binding of the agent to the SBP; and (c) comparing the amount of the specific binding in the test sample with the amount of specific binding in a control sample, wherein an increased or decreased amount of the specific binding in the test sample as compared to the control sample is diagnostic of a pathology. The agent can be, for example, an anti-SBP antibody, a SBP-associated-protein (SAP), or a SBP nucleic acid.

The invention also provides a method of diagnosing cancer or monitoring cancer therapy by contacting a test sample from a patient with a SBP-specific antibody. The invention additionally provides a method of assessing prognosis of patients with cancer comprising contacting a test sample from a patient with a SBP-specific antibody.

The invention additionally provides a method of diagnosing cancer, monitoring cancer therapy, or assessing prognosis of patients with cancer by contacting a test sample from a patient with a SBP oligonucleotide. The methods of the invention for diagnosing cancer, monitoring cancer therapy, or assessing prognosis of patients with cancer using a SBP-specific antibody or SBP oligonucleotide or nucleic acid can be used, for example, to segregate patients into a high risk group or a low risk group for predicting risk of metastasis or risk of failure to respond to therapy. Therefore, the methods of the invention can be advantageously used to determine the risk of metastasis in a cancer patient or as a prognostic indicator of survival in a cancer patient. One of ordinary skill in the art would appreciate that the prognostic indicators of survival for cancer patients suffering from stage I cancer can be different from those for cancer patients suffering from stage 1V cancer. For example, prognosis for stage I cancer patients can be oriented toward the likelihood of continued growth and/or metastasis of the cancer, whereas prognosis for stage IV cancer patients can be oriented toward the likely effectiveness of therapeutic methods for treating the cancer. Accordingly, the methods of the invention directed to measuring the level of or determining the presence of a SBP polypeptide or encoding nucleic acid can be used advantageously as a prognostic indicator for the presence or progression of a cancer or response to therapy.

In accordance with another embodiment of the present invention, there are provided diagnostic systems, preferably in kit form, comprising at least one invention nucleic acid or antibody in a suitable packaging material. The diagnostic kits containing nucleic acids are derived from the SEP-encoding nucleic acids described herein. In one embodiment, for example, the diagnostic nucleic acids are derived from SEQ ID NO:1 or 13 and can be oligonucleotides of the invention. Invention diagnostic systems are useful for assaying for the presence or absence of nucleic acid encoding SEP in either genomic DNA or mRNA.

A suitable diagnostic system includes at least one invention nucleic acid or antibody, as a separately packaged chemical reagent(s) in an amount sufficient for at least one assay. For a diagnostic kit containing nucleic acid of the invention, the kit will generally contain two or more nucleic acids. When the diagnostic kit is to be used in PCR, the kit will contain at least two oligonucleotides that can serve as primers for PCR. Those of skill in the art can readily incorporate invention nucleic probes and/or primers or invention antibodies into kit form in combination with appropriate buffers and solutions for the practice of the invention methods as described herein. A kit containing a SBP antibody can contain a reaction cocktail that provides the proper conditions for performing an assay, for example, an ELISA or other immunoassay, for determining the level of expression of a SBP polypeptide in a sample, and can contain control samples that contain known amounts of a SBP polypeptide and, if desired, a second antibody specific for the anti-SBP antibody.

The contents of the kit of the invention, for example, SBP nucleic acids or antibodies, are contained in packaging material, preferably to provide a sterile, contaminant-free environment. In addition, the packaging material contains instructions indicating how the materials within the kit can be employed both to detect the presence or absence of a particular SBP sequence or SBP polypeptide or to diagnose the presence of, or a predisposition for a condition associated with the presence or absence of SBP such as cancer. The instructions for use typically include a tangible expression describing the reagent concentration or at least one assay method parameter, such as the relative amounts of reagent and sample to be admixed, maintenance time periods for reagent/sample admixtures, temperature, buffer conditions, and the like.

The present invention also provides methods of identifying a compound that binds to a SBP, comprising the steps of:
(a) contacting said SBP with a test compound, under conditions that allow said SBP and compound to associate; and
(b) detecting a SBP:compound complex, thereby identifying a compound that binds to said SBP.

Exemplary methods of detecting a SBP:compound complexes are well-known in the art and include mass spectrometry, nuclear magnetic resonance (NMR), or virtual computational methods (See e.g., Shukur et al., 1996, *Science*, 274:1531–1534; Lengauer et al., 1996, *Current Opinions in Structural Biology*, 6:402–406; Choichet et al., 1991, *Journal of Molecular Biology*, 221:327–346; Cherfils et al., 1991, *Proteins*, 11:271–280; Palma et al., 2000, *Proteins*, 39:372–384; Eckert et al., 1999, Cell 99:103–115; Loo et al., 1999, *Med. Res. Rev.*, 19:307–319; Kramer et al., Nov. 7, 2000, *J. Biol. Chem.*, "Identification of the bile acid binding site of the ileal lipid binding protein (ILBP) by photoaffinity labeling, MALDI mass spectrometry and NMR structure," each of which are incorporated herein by reference in their entirety), and the like. Exemplary virtual computational methodology for detecting a SBP:compound complex preferably involves virtual docking of small-molecule compounds on a virtual representation of the SBP structure.

Also provided herein are methods of identifying a site on Survivin that interacts with SBP, said method comprising, constructing a plurality of Survivin mutants; contacting said Survivin mutants with SBP under conditions that permit SBP binding to native Survivin; and selecting a Survivin mutant that does not bind to SBP, thereby identifying a site on Survivin that interacts with SBP. Methods for constructing Survivin mutants are well-known in the art. Such mutants include single or multiple amino-acid deletions or substitutions, truncated mutants, and the like. For example, it is contemplated herein that several deletion mutants can be readily identified that overlap a region on Survivin that is required for SBP binding to Survivin. Once this region containing the SBP-binding site on Survivin is identified, this site can be used as a target in bioassays to identify compounds (e.g., drugs) that can bind to and modulate this site.

Techniques of structural biology can also be used to identify sites on survivin or SBP and Survivin required for their interactions, using techniques such as x-ray crystallography, photoaffinity labeling, MALDI mass spectrometry (see, e.g., Kramer et al., 2000, *J. Biol. Chem.*, supra,; Shukur et al., 1996, *Science*, supra, and the like); and high speed NMR using TROSY (transverse relaxation-optimized spectroscopy; see, e.g., Pervushin et al., 1997, *PNAS, USA*, 94:12366–12371, incorporated herein by reference in its entirety) methods. Thus, in accordance with another embodiment of the invention, there are provided methods of identifying a site on Survivin that interacts with SBP, said method comprising, contacting Survivin with SBP under conditions that permit SBP binding to native Survivin; and identifying a site on Survivin that interacts with SBP using at least one method selected from mass spectrometry, photoaffinity labeling, nuclear magnetic resonance (NMR), x-ray crystallography or virtual computational methodology. Exemplary virtual computational methods include, for example, protein—protein docking prediction (as described in, e.g., Lengauer et al., 1996, *Current Opinions in Structural Biology*, 6:402–406; Choichet et al., 1991, *Journal of Molecular Biology*, 221:327–346; Cherfils et al., 1991, *Proteins*, 11:271–280; Palma et al., 2000, *Proteins*, 39:372–384); and the like.

It is understood that modifications which do not substantially affect the activity of the various embodiments of this invention are also provided within the definition of the invention provided herein. Accordingly, the following examples are intended to illustrate but not limit the present invention.

MATERIALS AND METHODS

EXAMPLE 1

Plasmid Construction: Phospho-Mimic Survivin T34E Mutant

This experiment describes the construction of a Survivin T34E mutant.

In order to select for proteins that bind to the activated Survivin, a mutant version of Survivin was constructed which contains a Threonine 34 to Glutamic Acid (T34E) substitution intended to mimic the phophorylated state.

The mutant was generated by overlapping PCR from the plasmid pcDNA3-Survivin (Tamm, et al., 1998, Cancer Res., 58:5315–5320) using the following forward (F) and reverse (R) primers containing EcoRI and XhoI sites: Survivin T34E (1–34), 5'-CGAATTCATGGGTGC-CCCGACGTTG-3' SEQ ID NO:7) (F) and 5'-ATCCGCTC-CGGTTCGCAGG-3' (SEQ ID NO:8) (R); Survivin T34E (34–142), 5'-CCTGCGAACCGGAGCGGAT-3' (SEQ ID NO:9) (F) and 5'-GAGCTCGAGTTAATCCATGGCAGC-CAGCTGCTC-3' (SEQ ID NO:10) (R). The PCR products were digested with EcoRI and XhoI, then subcloned into the EcoRI and XhoI sites of pcDNA3 plasmid. The corresponding plasmid was sequenced to ensure that the T34E mutation had been created.

EXAMPLE 2

Yeast Two-Hybrid Screen of Survivin Binding Proteins

This experiment describes a yeast two-hybrid screening method to identify nucleic acid sequences coding for proteins that bind to the phospho-mimic Survivin T34E.

The human phospho-mimic Survivin T34E was subcloned into the EcoRI and XhoI sites of the pGilda plasmid and used as bait to screen a human fetal brain cDNA library. Library screening by the yeast two-hybrid method was performed as described in (Matsuzawa et al., 1998, *EMBO J.*, 17:2736–2747) using the pGilda plasmid encoding the human Survivin (T34E) protein as a bait, a fetal brain cDNA library (Invitrogen, Inc, Carlsbad, Calif.), and EGY191 strain *S. cerevisiae* (lex2op-LEU2). Cells were grown in either YPD medium with 1% yeast extract, 2% polypeptone, and 2% glucose, or in Burkholder's minimal medium (BMM) fortified with appropriate amino-acids. Transformations were performed by a LiCl method using 0.25 mg of pJG4-5-cDNA library DNA, and 5 mg of denatured salmon sperm carrier DNA. Clones that formed on Leu-deficient BMM plates containing 2% galactose/1% raffinose were transferred to BMM plates containing leucine and 2% glucose, and filter assays were performed for β-galactosidase measurements.

From an initial screen of 1×10⁷ transformants, 149 clones were identified that trans-activated the LEU2 reporter gene based on ability to grow on leucine-deficient media. Of these, 11 colonies were also positive for β-galactosidase. DNA sequencing analysis of one clone revealed the cDNA encoding SBP1 as described below.

EXAMPLE 3

Isolation of Full-Length Human SBP1 cDNAs

This experiment describes the molecular cloning of full-length human SBP1 cDNA.

To obtain the full-length cDNA of human SBP1, cDNAs were PCR-amplified from a fetal brain library cDNA library in the vector pJG4-5 (Invitrogen, Inc., Carlsbad, Calif.) by using a forward primer 5'-AGAATTCATGGAGCACTAC-CGGAAAGC-3' (SEQ ID NO:11) complementary to the vector and containing an EcoRI site and a reverse primer 5'-CAGCTCGAGTTACAAGTCTTCAC-GATCGGGTGTTTC-3' (SEQ ID NO:12) complementary to SBP and based on the sequences of EST database clones (NCBI ID: AW957916, AV705461, BE790325, AA313780, AA328484). The PCR products were digested with EcoRI and XhoI, then subcloned into the EcoRI and XhoI sites of pcDNA3 plasmid. The corresponding plasmid was sequenced.

The nucleotide sequence initially determined for SBP1 is set forth herein as SEQ ID NO:1. The corresponding amino acid sequence is set forth herein as SEQ ID NO:2. A typographical error in SEQ ID NO:1 was subsequently corrected. The correct sequence for the open reading frame encoding SBP1 is set forth herein as SEQ ID NO:13, and the corresponding amino acid sequence set forth herein as SEQ ID NO:14. SEQ ID NO:14 differs from SEQ ID NO:2 only at the six C-terminal residues, and is three amino acids shorter. SEQ ID NO:1 and SEQ ID NO:13, and likewise SEQ ID NO:2 and SEQ ID NO:14, are functionally equivalent molecules.

Figure 2:
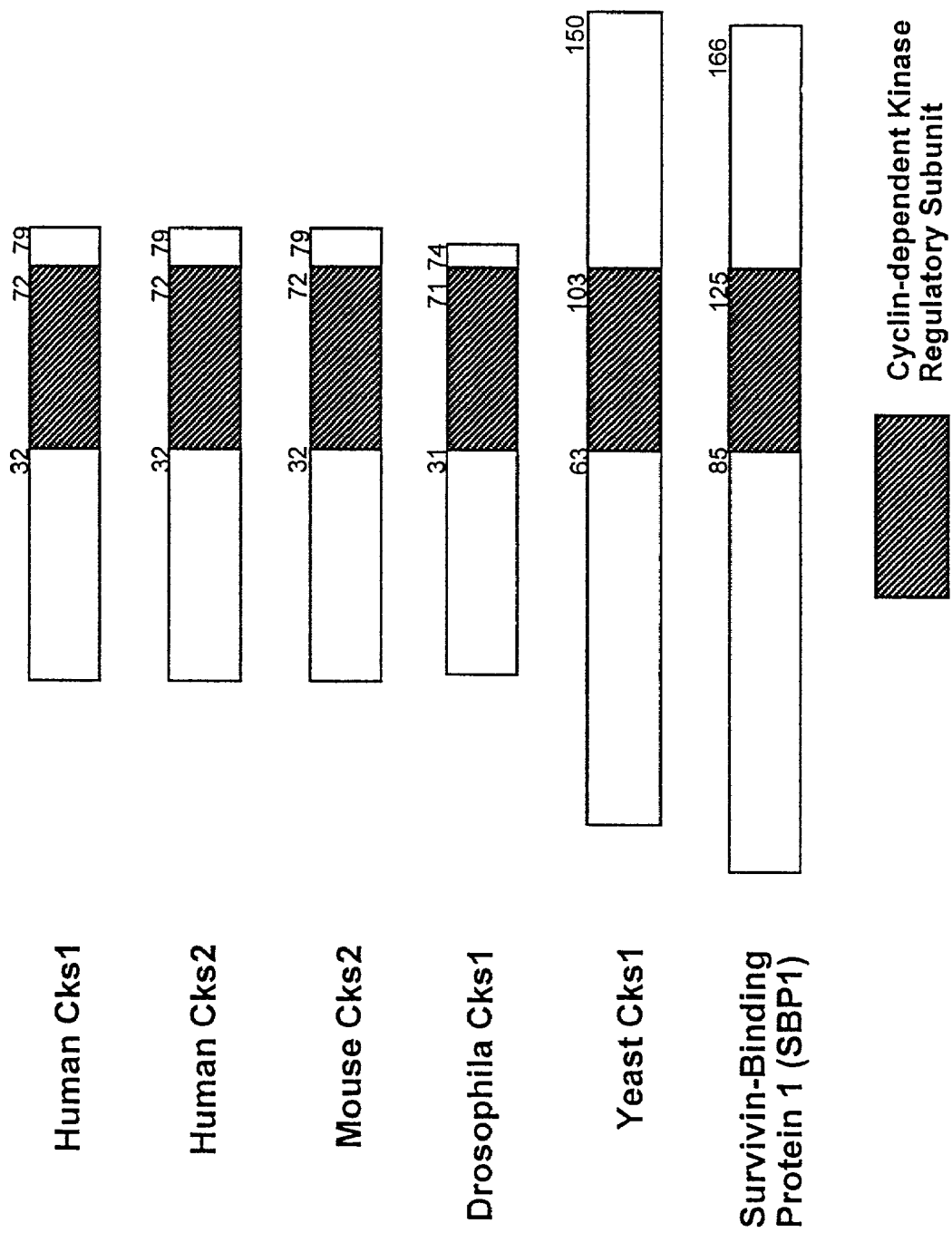
FIG. 2 shows the topologies of the known RS domain-containing proteins represented from various species, highlighting the locations of the RS domain (hatched).
Figure 3:
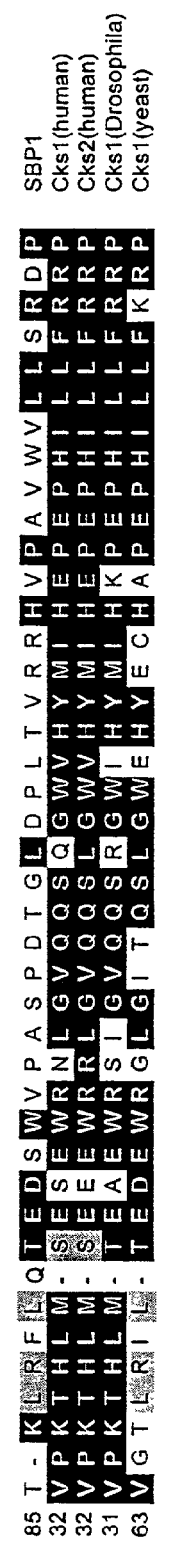

The region of the predicted amino acids 85 to 125 of SEQ ID NO: 2 or 14 of SBP1 were found to be homologous to cyclin-dependent kinase regulatory subunit (RS) domain, shown schematically in FIG. 1 and in comparison with the corresponding region of the cDNA that was isolated in the yeast two-hybrid screening assay. A schematic alignment of the SBP1 RS domain with those of human Cks1 and 2, *Drosophila* Cks1, yeast Cks1 and mouse Cks2 is shown in FIG. 2. The amino acid alignment is shown in FIG. 3, excluding the mouse (RS) sequence.

EXAMPLE 4

Yeast two-Hybrid Assay of Survivin T34E Mutant: SBP1 Binding Specificity

This experiment demonstrates the binding specificity of SBP1 to Survivin T34E in a yeast two-hybrid assay.

A plasmid (1 μg DNA) encoding a fusion protein of the LexA DNA-binding domain appended to the N-terminus of SBP1 was co-transformed into yeast strain EGY48 with 1 mg of pJG4-5 plasmid encoding fusion proteins of the B42 trans-activation domain fused to Survivin, Survivin T34E, Bcl-2, pro-caspase-9, XIAP, Bax, or Apaf-1. Bcl-2, pro-caspase-9, XIAP, Bax, and Apaf-1 are other inhibitors of apoptosis proteins. Transformed cells were grown on semi-solid media lacking leucine or containing leucine as a control (which resulted in equivalent amounts of growth for all transformants). Plasmid combinations that resulted in growth on leucine-deficient media within 4 days were scored as positive (+). β-galactosidase activity of each colony was tested by filter assay and scored as blue (+) versus white (−) after 60 minutes. Only the Survivin T34E scored positive for leucine and galactosidase activity, wild type Survivin, Bcl-2, caspase-9, XIAP, Bax and Apaf-1 scored negative under the conditions.

In view of the additional results described herein, these results indicate that SBP1 directly binds with Survivin T34E, more strongly than with wild type Survivin; and likely does not bind to Bcl-2, caspase-9, XIAP, Bax or Apaf-1.

EXAMPLE 5

In vitro Survivin: SBP1 Protein Interaction Assays.

This experiment describes the interaction of SBP1 with Survivin in vitro.

cDNAs encoding wild type Survivin or Survivin T34E was cloned into the EcoRI and XhoI sites of pGEX-4T-1 (Amersham-Pharmacia, Sweden), expressed in XL-1-blue cells (Stratagene, Inc., La Jolla, Calif.), and affinity-purified using glutathione-Sepharose, using methods essentially as described in (Xie et al., 1998, *Biochemistry*, 37:6410–6418). A GST-CD40 fusion protein was included as a negative control. Purified GST-fusion proteins (0.5–1.0 μg immobilized on 10–20 μl of glutathione beads) and 2.5 μl of rat reticulocyte lysates (TNT-Lysates; Promega, Inc., Madison, Wis.) containing $^{35}$S-labeled in vitro translated (IVT) SBP1 protein were incubated in 0.1 μl of HKMEN (10 mM HEPES [pH 7.2], 142 mM KCl, 5 mM MgCl$_2$, 2 mM EGTA, 0.1% NP-40) at 4° C. for 30 minutes. The beads were washed 3× with 1 ml HKMEN solution to remove unbound $^{35}$S-labeled IVT SBP1 protein, followed by boiling in 25 μl of Laemmli-SDS sample buffer to release and denature SBP1 bound to the matrix-bound GST-fusion protein. The eluted proteins were analyzed by SDS-PAGE (12%) and detected by fluorography.

Figure 4:
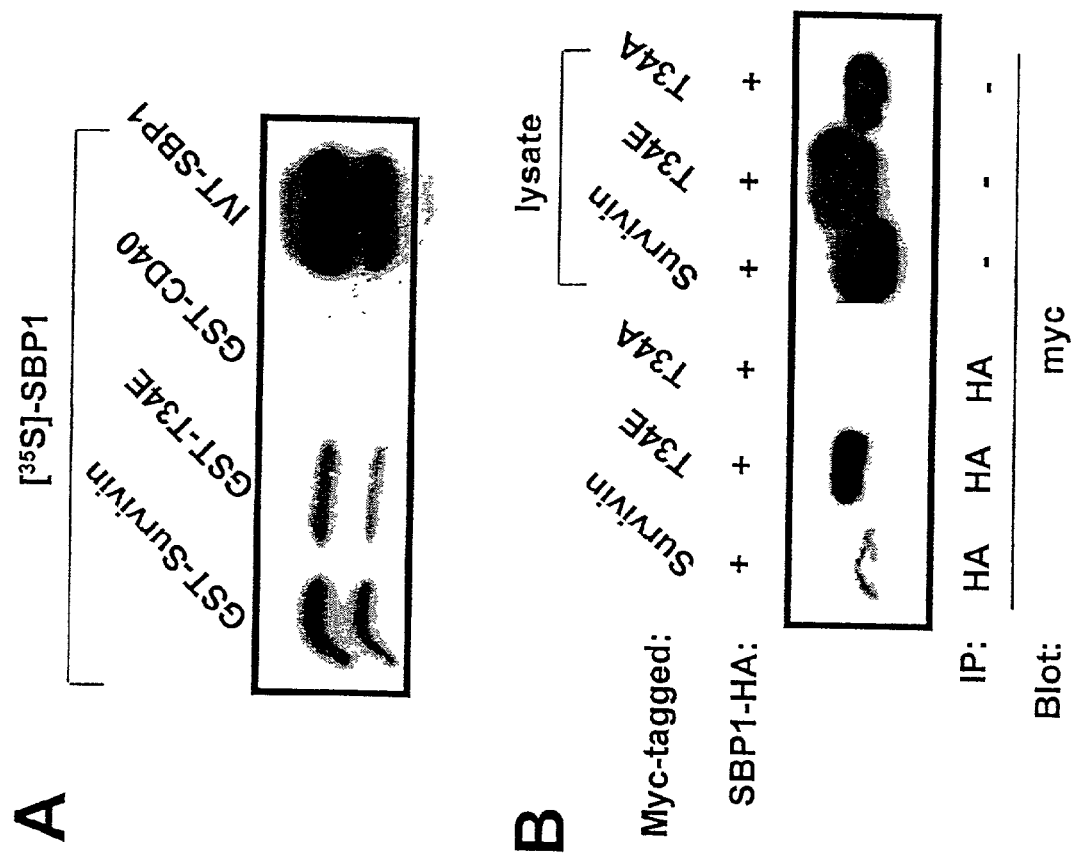
FIG. 4 shows an analysis of the interaction between SBP1 and Survivin. A: Labeled, in vitro-translated (IVT) SBP1 protein incubated with GST-Survivin, GST-T34E or GST-CD40 cytosolic domain proteins immobilized on glutathione-Sepharose and analyzed by SDS-PAGE/autoradiography. B: Myc-epitope tagged Survivin, T34E or T34A protein and hemagglutinin (HA)-tagged SBP1 protein were transiently expressed in 293T cells. Lysates were immunoprecipitated with ant-HA monoclonal antibody and analyzed by SDS-PAGE/immunoblotting using an anti-myc epitope monoclonal antibody.

The results are shown in FIG. 4A. The $^{35}$S-labeled IVT SBP1 bound to GST-Survivin and GST-Survivin T34E fusions, but not to the GST-CD40 fusion. Use of equivalent amounts of intact GST-fusion proteins and successful in vitro translation of each protein was confirmed by SDS-PAGE analysis using Coomassie staining or autoradiography, respectively.

EXAMPLE 6

Co-Immunoprecipitation Assays

This experiment demonstrates the intracellular interaction between Survivin and SBP1.

Two×10⁶ 293T cells in 100 mm plates were transiently transfected with 10 mg of pcDNA3-myc Survivin or its mutant (T34E or non-phosphorylatable T34A) and 10 μg of pcDNA3-HA-SBP1. Twenty-four hours later, cells were disrupted by sonication in 1 ml of RIPA solution containing 10 mM Tris-HCl (pH 7.4), 150 mM NaCl, 5 mM EDTA (pH 7.4), 1% Triton X-100, 1% DOC, 0.1% SDS, 0.1 μM PMSF, 5 μg/ml leupeptin, 1 μg/ml aprotinin and 1 μg/ml peptastatin. After preclearing with 20 μl of protein-G sepharose, immunoprecipitations were performed using 1 μg of anti-HA antibody (Roche) and 20 μl of protein-G sepharose to precipitate the HA-SBP1 fusion at 4° C. for 1 hour. After extensive washing in HKMEN solution, immune-complexes were analyzed by SDS-PAGE/immunoblotting using anti-myc antibody 9E10 followed by HRPase-conjugated goat anti mouse immunogloblin (Amersham-Pharmacia Inc., Sweden), and detected using an enhanced chemiluminescence (ECL) system (Amersham-Pharmacia, Inc.).

The results are shown in FIG. 4B. Immunoprecipitation of HA-SBP1 co-precipitates with myc-tagged Survivin T34E and, to a lesser extent, wild-type myc-tagged Survivin. The myc-tagged non-phosphorylatable mutant, Survivin T34A, did not co-precipitate with HA-SBP1. The myc-tagged Survivin and its mutants, T34A and T34E, were detectable in the lysates indicating their presence in the cell.

The results indicate that SBP1 protein binds to phosphomimic Survivin T34E and wild-type Survivin intracellularly, but not to a non-phosphorylatable mutant Survivin T34A.

EXAMPLE 7

Mapping of SBP1: Survivin T34E Interaction Domains.

This experiment demonstrates which domains of SBP1 allow binding to Survivin T34E.

To begin a dissection of the domains in SBP1 which allow this protein to bind to Survivin T34E, truncation mutants of SBP1 were prepared. In one mutant residues downstream of 91 were deleted, thus removing the C-terminal domain (SBP1-ΔC); in another mutant residues upstream of 90 were removed, thus eliminating the N-terminal domain (SBP1-ΔN); and in another mutant residues between 102 and 142 were removed, thus eliminating the possible cyclin dependent kinase regulatory subunit (RS) domain (SBP1-ΔRS). These constructs and Cks/Suc1 were labeled with $^{35}$S using rat reticulocyte lysates (TNT-Lysates; Promega, Inc., Madison, Wis.) and were incubated with purified GST-T34E fusion proteins in 0.1 ml of HKMEN (10 mM HEPES [pH 7.2], 142 mM KCl, 5 mM MgCl2, 2 mM EGTA, 0.1% NP-40) at 4° C. for 30 minutes. These mixtures were washed 3× with 1 ml HKMEN solution, followed by boiling in 25 μl of Laemmli-SDS sample buffer. The eluted proteins were analyzed by SDS-PAGE (12%) and detected by fluorography. Use of equivalent amounts of intact GST-fusion proteins and successful IVT of each protein was confirmed by SDS-PAGE analysis using Coomassie staining or autoradiography, respectively.

Figure 5:
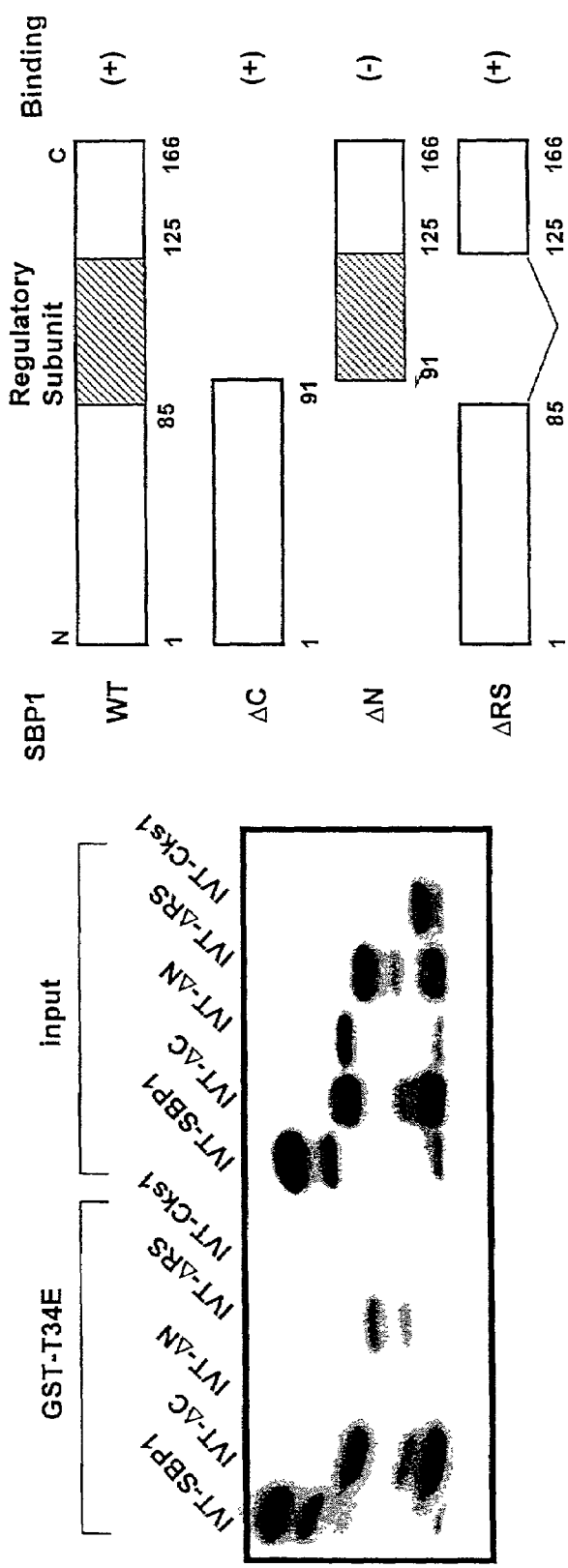
FIG. 5 shows SBP1 Survivin-binding domain analysis. IVT, labeled full-length SBP1, SBP1 lacking C-terminal domain (ΔC), SBP1 lacking the N-terminal domain (ΔN) and SBP1 lacking cyclin-dependent kinase regulatory subunit (ΔRS), or full-length Cks1/Suc1 incubated with GST-T34E and analyzed by SDS-PAGE autoradiography.

The results are shown in FIG. 5, and indicate that GST-T34E associated with IVT-SBP1, ΔC and ΔRS but not with IVT-ΔN in vitro. Therefore, a region within the N-terminal domain, between amino acid residues 1 and 90, is necessary for SBP1 to bind Survivin.

EXAMPLE 8

Kinase Assay

This example demonstrates that SBP1 enhances cyclin B1/cdc2 kinase activity in vitro.

HeLa cells were grown in 10-cm plates in high-glucose DMEM medium containing 10% fetal calf serum, 1 mM L-glutamine, and antibiotics in a humidified incubator at 37° C. until the cultures reached about 50% confluence. Cells were harvested and disrupted by sonication in 1 ml RIPA solution containing 10 mM Tris-HCl (pH 7.4), 150 mM NaCl, 5 mM EDTA (pH 7.4), 1% Triton X-100, 1% DOC, 0.1% SDS, 0.1 μM PMSF, 5 μg/ml leupeptin, 1 μg/ml aprotinin and 1 μg/ml peptastatin. Immunoprecipitations were performed using 4 μg of anti-Cyclin B1 (Upstate Biotechnology, Lake Placid, N.Y.) at 4° C. overnight, with precipitation of the immune complexes by addition of 100 μl of washed Protein G agarose bead slurry. Immunoprecipitates were mixed with 10 μl kinase buffer containing 50 μM ATP, 10 μCi [γ-$^{32}$P]ATP, 20 μg histone H1 and 10 μg His-CKS1 or GST-SBP1. His-CKS1 is known to phosphorylate cyclin B1 and is therefore included as a positive control. Samples were separated by SDS gel electrophoresis and phosphorylated bands were visualized by autoradiography. Equal protein loading was confirmed by Coomassie blue staining of the gel.

Figure 6:
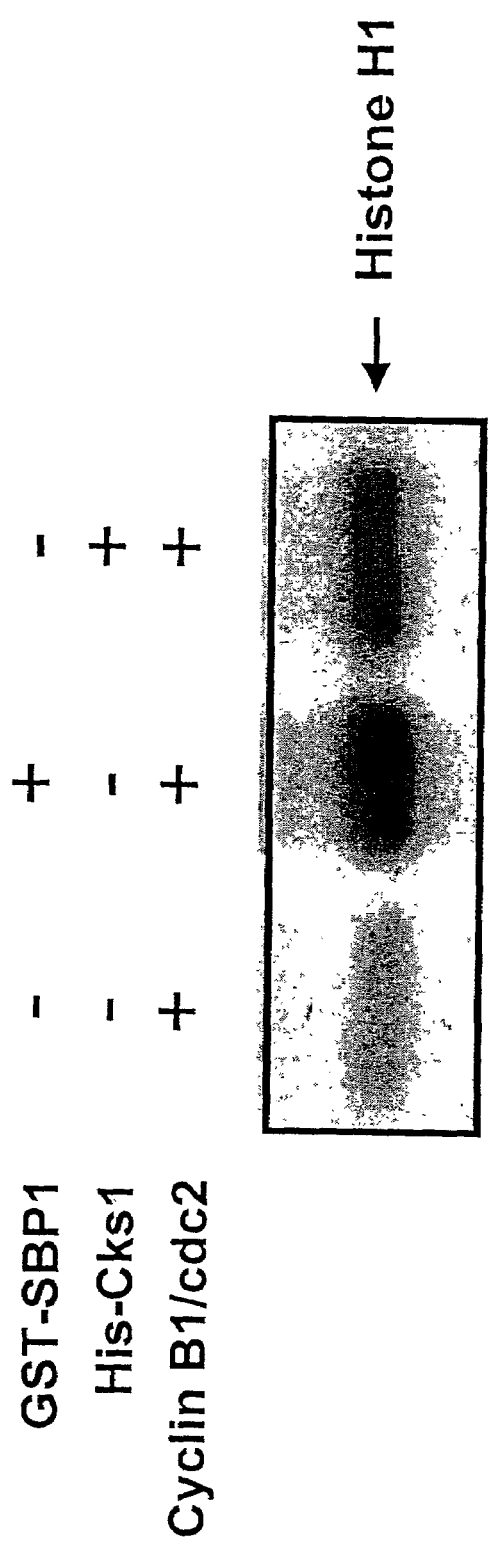
FIG. 6 shows SBP1 enhances cyclin B1/cdc2 kinase activity in vitro. Cell-free extracts immunoprecipitated with anti-cyclin B1 antibody were assayed for histone H1 phosphorylation in the presence of His-CKS1 or GST-SBP1 then subjected to SDS-PAGE/autoradiography.

The results are shown in FIG. 6 and indicate that Histone H1 is not phosphorylated in the presence of immunoprecipitated cyclin B1/cdc2 alone, but is phosphorylated in the added presence of His-Cks 1, and to greater extent in the added presence of SBP1. The results indicate that SBP1 enhances cyclin B1/cdc2 kinase activity in vitro, and does so more strongly than Cks/Suc1.

While the invention has been described in detail with reference to certain preferred embodiments thereof, it will be understood that modifications and variations are within the spirit and scope of that which is described and claimed.

What is claimed is:

1. An isolated SBP1 polypeptide consisting of the polypeptide encoded by a nucleic acid molecule selected from the group consisting of:
   (a) the nucleic acid molecule encoding the polypeptide consisting of amino acids 1–91 of SEO ID NO: 14, wherein said polypeptide binds Survivin: and
   (b) the nucleic acid molecule encoding the polypeptide consisting of amino acids 85–125 of SEQ ID NO:14, wherein said polypeptide enhances cyclin B 1/cdc2 kinase activity.

2. The SBP1 polypeptide of claim 1, wherein said polypeptide comprises consists of the amino acid sequence set forth as amino acids 1–91 of SEQ ID NO: 14.

3. The SBP1 polypeptide of claim 1, wherein said polypeptide comprises consists of the amino acid sequence set forth as amino acids 85–125 of SEQ ID NO: 14.

4. A therapeutic composition comprising a pharmaceutically acceptable carrier and a SBP1 polypeptide consisting of
   (a) the amino acid sequence consisting of amino acids 1–91 of SEQ ID NO: 14, wherein said SBP polypeptide binds Survivin; or
   (b) the amino acid sequence consisting of amino acids 85–125 of SEQ ID NO:14, wherein said SBP1 polypeptide enhances cyclin B1/cdc2 kinase activity.

5. An isolated chimeric protein comprising a heterologous protein fused to a SBP1 domain selected from the group consisting of the Survivin-binding domain consisting of amino acids 1–91 of SEQ ID NO:14 and a cyclin-dependent kinase regulatory domain consisting of amino acids 85–125 of SEQ ID NO:14.

6. The composition of claim 4, wherein said SBP1 polypeptide consists of amino acids 1–91 of SEQ ID NO:14.

7. The composition of claim 4, wherein said SBP1 polypeptide consists of amino acids 85–125 of SEQ ID NO:14.

8. The chimeric protein of claim 5, wherein said SBP1 domain is the Survivin-binding domain consisting of amino acids 1–91 of SEQ ID NO: 14.

9. The chimeric protein of claim 5, wherein said SBP1 domain is the cyclin-dependent kinase regulatory domain consisting of amino acids 85–125 of SEQ ID NO: 14.

* * * * *

SEQUENCE LISTING

```
<160> NUMBER OF SEQ ID NOS: 14

<210> SEQ ID NO 1
<211> LENGTH: 645
<212> TYPE: DNA
<213> ORGANISM: Homo sapiens
<220> FEATURE:
<221> NAME/KEY: CDS
<222> LOCATION: (145)...(642)

<400> SEQUENCE: 1
ttgggtaccg ggcccccct cgaggtcgac ggtatcgata agcttgatat cgaattcggc      60
acgagccgcg cgccatcttg gctccggatc gtgcgtgagg aggcttcgtg ggcagcgaga     120
gtcacagaca agacagcaag cagg atg gag cac tac cgg aaa gct ggc tct       171
                          Met Glu His Tyr Arg Lys Ala Gly Ser
                           1               5
```

```
gta gag ctc cca gcg cct tcc cca atg ccc cag cta cct cct gat acc      219
Val Glu Leu Pro Ala Pro Ser Pro Met Pro Gln Leu Pro Pro Asp Thr
 10              15                  20                  25 ctt gag atg cgg gtc cga gat ggc agc aaa att cgc aac ctg ctg ggg      267
Leu Glu Met Arg Val Arg Asp Gly Ser Lys Ile Arg Asn Leu Leu Gly
             30                  35                  40 ttg gct ctg ggt cgg ttg gag ggc ggc agt gct cgg cat gta gtg ttc      315
Leu Ala Leu Gly Arg Leu Glu Gly Gly Ser Ala Arg His Val Val Phe
         45                  50                  55 tca ggt tct ggc agg gct gca gga aag gct gtc agc tgc gct gag att      363
Ser Gly Ser Gly Arg Ala Ala Gly Lys Ala Val Ser Cys Ala Glu Ile
     60                  65                  70 gtc aag cgg cgg gtc cca ggc ctg cac cag ctc acc aag cta cgt ttc      411
Val Lys Arg Arg Val Pro Gly Leu His Gln Leu Thr Lys Leu Arg Phe
 75                  80                  85 ctt cag act gag gac agc tgg gtc cca gcc tca cct gac aca ggg cta      459
Leu Gln Thr Glu Asp Ser Trp Val Pro Ala Ser Pro Asp Thr Gly Leu
 90                  95                 100                 105 gac ccc ctc aca gtg cgc cgc cat gtg cct gca gtg tgg gtg ctg ctc      507
Asp Pro Leu Thr Val Arg Arg His Val Pro Ala Val Trp Val Leu Leu
                110                 115                 120 agc cgg gac ccc ctg gac ccc aat gag tgt ggt tac caa ccc cca gga      555
Ser Arg Asp Pro Leu Asp Pro Asn Glu Cys Gly Tyr Gln Pro Pro Gly
             125                 130                 135 gca ccc cct ggc ctg ggt tcc atg ccc agc tcc agc tgt ggc cct cgt      603
Ala Pro Pro Gly Leu Gly Ser Met Pro Ser Ser Ser Cys Gly Pro Arg
         140                 145                 150 tcc cga aga agg ctc gag aca ccc gat cgt gaa gac ttg tga              645
Ser Arg Arg Arg Leu Glu Thr Pro Asp Arg Glu Asp Leu
     155                 160                 165

<210> SEQ ID NO 2
<211> LENGTH: 166
<212> TYPE: PRT
<213> ORGANISM: Homo sapiens

<400> SEQUENCE: 2

Met Glu His Tyr Arg Lys Ala Gly Ser Val Glu Leu Pro Ala Pro Ser
 1               5                  10                  15

Pro Met Pro Gln Leu Pro Pro Asp Thr Leu Glu Met Arg Val Arg Asp
             20                  25                  30

Gly Ser Lys Ile Arg Asn Leu Leu Gly Leu Ala Leu Gly Arg Leu Glu
         35                  40                  45

Gly Gly Ser Ala Arg His Val Val Phe Ser Gly Ser Gly Arg Ala Ala
     50                  55                  60

Gly Lys Ala Val Ser Cys Ala Glu Ile Val Lys Arg Arg Val Pro Gly
 65                  70                  75                  80

Leu His Gln Leu Thr Lys Leu Arg Phe Leu Gln Thr Glu Asp Ser Trp
                 85                  90                  95

Val Pro Ala Ser Pro Asp Thr Gly Leu Asp Pro Leu Thr Val Arg Arg
            100                 105                 110

His Val Pro Ala Val Trp Val Leu Leu Ser Arg Asp Pro Leu Asp Pro
        115                 120                 125

Asn Glu Cys Gly Tyr Gln Pro Pro Gly Ala Pro Pro Gly Leu Gly Ser
    130                 135                 140

Met Pro Ser Ser Ser Cys Gly Pro Arg Ser Arg Arg Arg Leu Glu Thr
145                 150                 155                 160
```

-continued

Pro Asp Arg Glu Asp Leu
            165

<210> SEQ ID NO 3
<211> LENGTH: 41
<212> TYPE: PRT
<213> ORGANISM: Homo sapiens

<400> SEQUENCE: 3

Val Pro Lys Thr His Leu Met Ser Glu Ser Glu Trp Arg Asn Leu Gly
1               5                   10                  15

Val Gln Gln Ser Gln Gly Trp Val His Tyr Met Ile His Glu Pro Glu
            20                  25                  30

Pro His Ile Leu Leu Phe Arg Arg Pro
        35                  40

<210> SEQ ID NO 4
<211> LENGTH: 41
<212> TYPE: PRT
<213> ORGANISM: Homo sapiens

<400> SEQUENCE: 4

Val Pro Lys Thr His Leu Met Ser Glu Glu Glu Trp Arg Arg Leu Gly
1               5                   10                  15

Val Gln Gln Ser Leu Gly Trp Val His Tyr Met Ile His Glu Pro Glu
            20                  25                  30

Pro His Ile Leu Leu Phe Arg Arg Pro
        35                  40

<210> SEQ ID NO 5
<211> LENGTH: 41
<212> TYPE: PRT
<213> ORGANISM: Drosophila melanogaster

<400> SEQUENCE: 5

Val Pro Lys Thr His Leu Met Thr Glu Ala Glu Trp Arg Ser Ile Gly
1               5                   10                  15

Val Gln Gln Ser Arg Gly Trp Ile His Tyr Met Ile His Lys Pro Glu
            20                  25                  30

Pro His Ile Leu Leu Phe Arg Arg Pro
        35                  40

<210> SEQ ID NO 6
<211> LENGTH: 41
<212> TYPE: PRT
<213> ORGANISM: Saccharomyces cerevisiae

<400> SEQUENCE: 6

Val Gly Thr Leu Arg Ile Leu Thr Glu Asp Glu Trp Arg Gly Leu Gly
1               5                   10                  15

Ile Thr Gln Ser Leu Gly Trp Glu His Tyr Glu Cys His Ala Pro Glu
            20                  25                  30

Pro His Ile Leu Leu Phe Lys Arg Pro
        35                  40

<210> SEQ ID NO 7
<211> LENGTH: 25
<212> TYPE: DNA
<213> ORGANISM: Artificial Sequence
<220> FEATURE:
<223> OTHER INFORMATION: primer

```
<400> SEQUENCE: 7
cgaattcatg ggtgccccga cgttg                                           25

<210> SEQ ID NO 8
<211> LENGTH: 19
<212> TYPE: DNA
<213> ORGANISM: Artificial Sequence
<220> FEATURE:
<223> OTHER INFORMATION: primer

<400> SEQUENCE: 8
atccgctccg gttcgcagg                                                  19

<210> SEQ ID NO 9
<211> LENGTH: 19
<212> TYPE: DNA
<213> ORGANISM: Artificial Sequence
<220> FEATURE:
<223> OTHER INFORMATION: primer

<400> SEQUENCE: 9
cctgcgaacc ggagcggat                                                  19

<210> SEQ ID NO 10
<211> LENGTH: 33
<212> TYPE: DNA
<213> ORGANISM: Artificial Sequence
<220> FEATURE:
<223> OTHER INFORMATION: primer

<400> SEQUENCE: 10
gagctcgagt taatccatgg cagccagctg ctc                                  33

<210> SEQ ID NO 11
<211> LENGTH: 27
<212> TYPE: DNA
<213> ORGANISM: Artificial Sequence
<220> FEATURE:
<223> OTHER INFORMATION: primer

<400> SEQUENCE: 11
agaattcatg gagcactacc ggaaagc                                         27

<210> SEQ ID NO 12
<211> LENGTH: 36
<212> TYPE: DNA
<213> ORGANISM: Artificial Sequence
<220> FEATURE:
<223> OTHER INFORMATION: primer

<400> SEQUENCE: 12
cagctcgagt tacaagtctt cacgatcggg tgtttc                               36

<210> SEQ ID NO 13
<211> LENGTH: 492
<212> TYPE: DNA
<213> ORGANISM: Homo sapiens
<220> FEATURE:
<221> NAME/KEY: CDS
<222> LOCATION: (1)...(489)

<400> SEQUENCE: 13 atg gag cac tac cgg aaa gct ggc tct gta gag ctc cca gcg cct tcc       48
Met Glu His Tyr Arg Lys Ala Gly Ser Val Glu Leu Pro Ala Pro Ser
 1               5                  10                  15
```

```
cca atg ccc cag cta cct cct gat acc ctt gag atg cgg gtc cga gat      96
Pro Met Pro Gln Leu Pro Pro Asp Thr Leu Glu Met Arg Val Arg Asp
        20                  25                  30 ggc agc aaa att cgc aac ctg ctg ggg ttg gct ctg ggt cgg ttg gag     144
Gly Ser Lys Ile Arg Asn Leu Leu Gly Leu Ala Leu Gly Arg Leu Glu
    35                  40                  45 ggc ggc agt gct cgg cat gta gtg ttc tca ggt tct gcc agg gct gca     192
Gly Gly Ser Ala Arg His Val Val Phe Ser Gly Ser Gly Arg Ala Ala
50                  55                  60 gga aag gct gtc agc tgc gct gag att gtc aag cgg cgg gtc cca ggc     240
Gly Lys Ala Val Ser Cys Ala Glu Ile Val Lys Arg Arg Val Pro Gly
65                  70                  75                  80 ctg cac cag ctc acc aag cta cgt ttc ctt cag act gag gac agc tgg     288
Leu His Gln Leu Thr Lys Leu Arg Phe Leu Gln Thr Glu Asp Ser Trp
                85                  90                  95 gtc cca gcc tca cct gac aca ggg cta gac ccc ctc aca gtg cgc cgc     336
Val Pro Ala Ser Pro Asp Thr Gly Leu Asp Pro Leu Thr Val Arg Arg
            100                 105                 110 cat gtg cct gca gtg tgg gtg ctg ctc agc cgg gac ccc ctg gac ccc     384
His Val Pro Ala Val Trp Val Leu Leu Ser Arg Asp Pro Leu Asp Pro
        115                 120                 125 aat gag tgt ggt tac caa ccc cca gga gca ccc cct ggc ctg ggt tcc     432
Asn Glu Cys Gly Tyr Gln Pro Pro Gly Ala Pro Pro Gly Leu Gly Ser
130                 135                 140 atg ccc agc tcc agc tgt ggc cct cgt tcc cga aga agg gct cga gac     480
Met Pro Ser Ser Ser Cys Gly Pro Arg Ser Arg Arg Arg Ala Arg Asp
145                 150                 155                 160 acc cga tcg tga                                                     492
Thr Arg Ser
```

<210> SEQ ID NO 14
<211> LENGTH: 163
<212> TYPE: PRT
<213> ORGANISM: Homo sapiens

<400> SEQUENCE: 14

```
Met Glu His Tyr Arg Lys Ala Gly Ser Val Glu Leu Pro Ala Pro Ser
1               5                   10                  15

Pro Met Pro Gln Leu Pro Pro Asp Thr Leu Glu Met Arg Val Arg Asp
            20                  25                  30

Gly Ser Lys Ile Arg Asn Leu Leu Gly Leu Ala Leu Gly Arg Leu Glu
        35                  40                  45

Gly Gly Ser Ala Arg His Val Val Phe Ser Gly Ser Gly Arg Ala Ala
    50                  55                  60

Gly Lys Ala Val Ser Cys Ala Glu Ile Val Lys Arg Arg Val Pro Gly
65                  70                  75                  80

Leu His Gln Leu Thr Lys Leu Arg Phe Leu Gln Thr Glu Asp Ser Trp
                85                  90                  95

Val Pro Ala Ser Pro Asp Thr Gly Leu Asp Pro Leu Thr Val Arg Arg
            100                 105                 110

His Val Pro Ala Val Trp Val Leu Leu Ser Arg Asp Pro Leu Asp Pro
        115                 120                 125

Asn Glu Cys Gly Tyr Gln Pro Pro Gly Ala Pro Pro Gly Leu Gly Ser
    130                 135                 140

Met Pro Ser Ser Ser Cys Gly Pro Arg Ser Arg Arg Arg Ala Arg Asp
145                 150                 155                 160

Thr Arg Ser
```